(12) United States Patent
Gutman et al.

(10) Patent No.: US 7,157,590 B2
(45) Date of Patent: Jan. 2, 2007

(54) PROCESS FOR THE PREPARATION OF 17-PHENYL-18,19,20-THINOR-PGF 2A AND ITS DERIVATIVES

(75) Inventors: Arie Gutman, Haifa (IL); Gennady Nisnevich, Haifa (IL); Marina Etinger, Nesher (IL); Igor Zaltzman, Haifa (IL); Lev Yudovitch, Haifa (IL); Boris Pertsikov, Nesher (IL)

(73) Assignee: Finetech Laboratories Ltd., Haifa (IL)

( * ) Notice: Subject to any disclaimer, the term of this patent is extended or adjusted under 35 U.S.C. 154(b) by 63 days.

(21) Appl. No.: 10/478,849

(22) PCT Filed: May 3, 2002

(86) PCT No.: PCT/IL02/00422

§ 371 (c)(1),
(2), (4) Date: Apr. 28, 2004

(87) PCT Pub. No.: WO02/096868

PCT Pub. Date: Dec. 5, 2002

(65) Prior Publication Data

US 2004/0171873 A1     Sep. 2, 2004

(30) Foreign Application Priority Data

May 31, 2001   (IL) ..................................... 143477

(51) Int. Cl.
   *C07C 51/36*   (2006.01)
(52) U.S. Cl. ..................... 554/142; 554/141; 554/159; 554/222; 549/312; 549/465; 549/466
(58) Field of Classification Search ................ 554/141, 554/142, 159, 221, 222; 549/465, 466, 312
See application file for complete search history.

(56) References Cited

U.S. PATENT DOCUMENTS

| | | | |
|---|---|---|---|
| 3,931,279 A | 1/1976 | Nelson | |
| 4,346,228 A | 8/1982 | Skuballa et al. | |
| 5,352,708 A | * 10/1994 | Woodward et al. | ......... 514/729 |
| 5,688,819 A | * 11/1997 | Woodward et al. | ......... 514/357 |
| 5,698,733 A | 12/1997 | Hellberg et al. | |
| 6,689,901 B1 | 2/2004 | Henegar | |

FOREIGN PATENT DOCUMENTS

| | | |
|---|---|---|
| EP | 0850926 | 7/1998 |
| EP | 0930296 | 7/1999 |
| WO | WO 93/00329 | 7/1993 |
| WO | WO 95/28729 | 12/1995 |
| WO | WO 01/55101 | 8/2001 |
| WO | WO 01/87816 | 11/2001 |

OTHER PUBLICATIONS

Bahram Resul, et al (1993) "Phenyl-Substituted Prostaglandins: Potent and Selective Antigalucoma Agents." J Med Chem, 36, 243-248.
Chem Abstr, CAN 117:111373, AN 1992 511373.
DeLong, et al, (1993) Bioorg. Med. Chem Lett, 2000, v 10, 1519.
Disselnkoetter, et al, (1982) Liebigs Ann Chem, 150.
Dolence, et al, (1987) Tetrahedron Lett v.28, 43.
Exp Eye Res., 2004, v.78, 767.
J Ocular Pharmacol, Therap, 2003, v. 19, 501.
Magerlein B J et al "Synthesis of 17-Phenyl-18, 19,20-Trinorprostaglandins" Prosraglandins Jan. 1975 vol. 9 No. 1.

* cited by examiner

*Primary Examiner*—Deborah D. Carr
(74) *Attorney, Agent, or Firm*—Pearl Cohen Zedek Latzer LLP; Mark S. Cohen

(57) ABSTRACT

The present invention provides a new and effective process for the synthesis of 17-phenyl-18,19,20-trinor-PGF$_{2\alpha}$ and its derivatives, including the anti-glaucoma drugs Bimatoprost and Latanoprost. The benefit of the present invention rises inter alia from the fact that a major intermediate involved in the synthesis of the above compounds may be isolated from a mixture containing also an undesired isomer, by crystallization. In addition, the undesired isomer may be oxidized to give the starting compound, which is then recycled.

14 Claims, No Drawings

PROCESS FOR THE PREPARATION OF 17-PHENYL-18,19,20-THINOR-PGF 2A AND ITS DERIVATIVES

FIELD OF THE INVENTION

This invention relates to a novel process for the preparation of 17-phenyl-18,19,20-trinor-$PGF_{2\alpha}$ and its derivatives.

BACKGROUND OF THE INVENTION

17-Phenyl-18,19,20-trinor-$PGF_{2\alpha}$ and its derivatives of Formula [1b]:

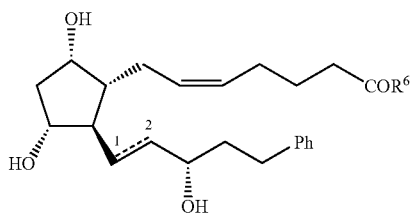

wherein
the bond between carbon 1 and 2 is either a single bond ($C^1$—$C^2$) or a double bond ($C^1$=$C^2$), and $R^6$ is selected from the group consisting of alkoxy and alkylamino, are synthetic structural analogs of prostaglandins with ocular hypotensive activity (B. Resul et al., J. Med. Chem., 1993, 36, 243 and U.S. Pat. No. 5,688,819). 17-Phenyl-18,19, 20-trinor-$PGF_{2\alpha}$ N-ethylamide (Bimatoprost) (New Drug Application (NDA) 21-275 published by the FDA) and 13,14-dihydro-17-phenyl-18,19,20-trinor-$PGF_{2\alpha}$ isopropyl ester (Latanoprost) (The Merck Index, 12th Ed., 5787) are believed to lower intraocular pressure (IOP) in humans by increasing outflow of aqueous humor through both the trabecular meshwork and uveoscleral routs. Elevated IOP presents a major risk factor for glaucomatous field loss. The higher the level of IOP, the greater the likelihood of optic nerve damage and visual field loss.

The known methods for the synthesis of compounds of formula [1b] (see U.S. Pat. Nos. 3,931,279; 5,223,537; 5,698,733; and 5,688,819; WO95/26729, Prostaglandins, v. 9, 5 1975, J. Med. Chem., 1993, 36, 243) are shown in Scheme 1 below and include the stages of reducing the carbonyl group of compound [4] to yield a mixture of compounds [5] and [6a], separating the by-product [6a] from the desired compound [5] ($C^1$=$C^2$ and $R^2$=H) by column chromatography, and reducing the compound [5] ($C^1$=$C^2$ and $R^2$=H) (optionally, after OH-deprotecting/protecting procedures and/or $C^1$=$C^2$ double bond catalytic hydrogenation) with diisobutylaluminum hydride at temperature −70 to −80° C. to give compound [11], reacting the compound [11] with a metal salt of 5-(triphenylphosphoranylidene) pentanoic acid to obtain compound [1a] which yield (optionally after deprotecting the hydroxyl groups) compound [1b]:

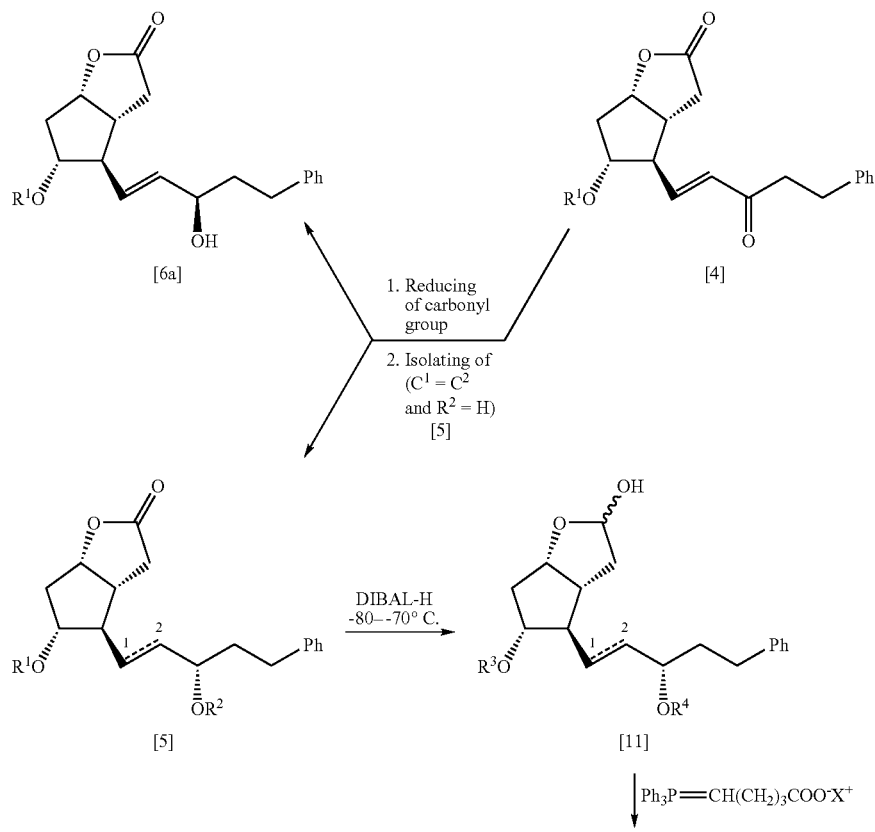

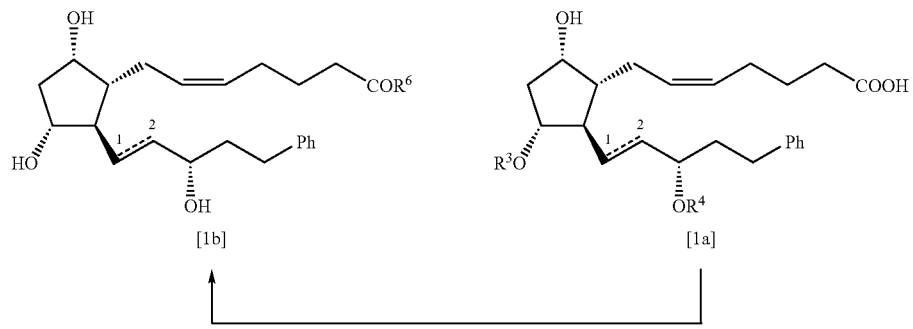

However, this method is problematic since (a) the by-product [6a] is not regenerated; (b) it is difficult to separate the by-product [6a] from the desired compound [5] ($C^1$=$C^2$ and $R^2$=H) and (c) it is difficult to scale-up the highly exothermic reduction of [5] ($C^1$=$C^2$ and $R^2$=H) with DIBAL-H at such low temperature conditions.

SUMMARY OF THE INVENTION

It is an object of this invention to provide a novel process for the preparation of 17-phenyl-18,19,20-trinor-PGF$_{2\alpha}$ and its derivatives in good yield, in large amounts and with desired purity.

It is a further object of this invention to provide novel intermediates for the above process.

The above objects are achieved by the present invention, which provides a process for the preparation of 17-phenyl-18,19,20-trinor-PGF$_{2\alpha}$ and its derivatives of Formula [1b]

[1b]

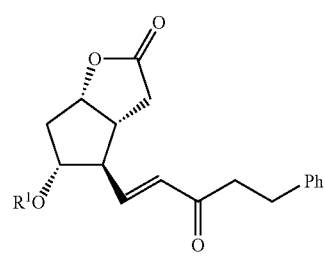

wherein
the bond between carbons 1 and 2 is either a single bond ($C^1$—$C^2$) or a double bond ($C^1$=$C^2$), and
$R^6$ is selected from the group consisting of alkoxy and alkylamino; such process comprising:

(a) stereoselective reduction of the carbonyl group of the compound [4]

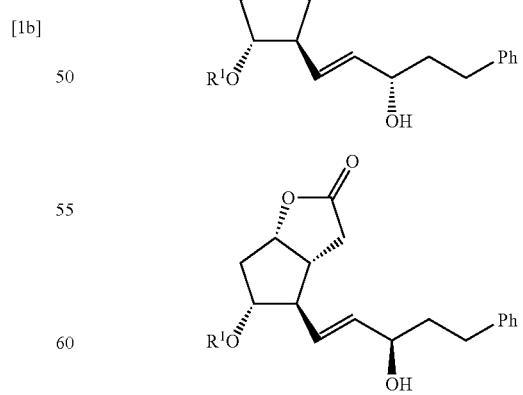

to yield a mixture of compounds of formulae [5a] and [6a], where [5a] is the predominant isomer, which are subsequently converted into a mixture of compounds of formulae [5] ($C^1$=$C^2$) and [6]:

[5]

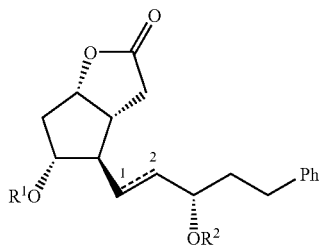

[6]

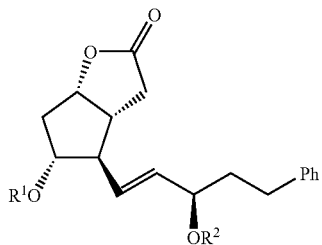

followed by isolation of the compound [5] ($C^1=C^2$) from the mixture and, if desired, hydrogenation of the double bond $C^1=C^2$ between carbons 1 and 2 of the compound [5] ($C^1=C^2$) in the presence of a catalyst to give the compound [5] ($C^1—C^2$) where the bond between carbons 1 and 2 is a single bond;

where one of $R^1$ and $R^2$ is an arylcarbonyl group and the other one is selected from the group consisting of arylcarbonyl, acyl, trialkylsilyl, dialkylarylsilyl, 1-alkoxyalkyl, unsubstituted and alkyl-substituted tetrahydro-2H-pyran-2-yl and tetrahydrofuran-2-yl;

(b) converting compound [6] from the mother liquor of step (a) into the compound [6a], oxidizing the hydroxyl group of the compound [6a] to yield the compound [4] and recycling the compound [4] to step (a);

(c) reducing the compound [5] obtained in step (a) with diisobutylaluminum hydride at a temperature range from −20 to +20° C. followed by hydrolysis of the obtained reaction mixture under basic conditions to give the compound [11],

[11]

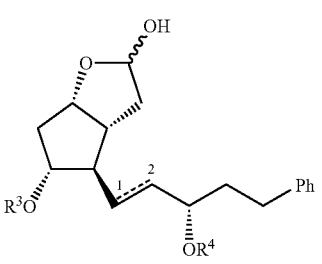

wherein the bond between carbons 1 and 2 is either a single bond ($C^1—C^2$) or a double bond ($C^1=C^2$);

$R^3$ is hydrogen when $R^1$ is acyl and is equal to $R^1$ when it is trialkylsilyl, dialkylarylsilyl, 1-alkoxyalkyl, unsubstituted or alkyl-substituted tetrahydro-2H-pyran-2-yl or tetrahydrofuran-2-yl;

$R^4$ is hydrogen when $R^2$ is acyl and is equal to $R^2$ when it is trialkylsilyl, dialkylarylsilyl, 1-alkoxyalkyl, unsubstituted or alkyl-substituted tetrahydro-2H-pyran-2-yl or tetrahydrofuran-2-yl and (d) reacting compound [11] with a metal salt of 5-(triphenylphosphoranylidene)pentanoic acid, to obtain the compound of formula [1a]:

[1a]

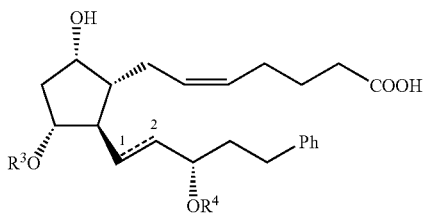

and (e) deriving the carboxyl group of the compound [1a], optionally, after deprotecting the hydroxyl groups, to give the desired compound [1b].

Some of the new compounds [5] ($R^1$=PPB and $R^2$=THP), which are obtained as intermediates in the process of the present invention, may be purified by crystallization from organic solvents. These new compounds represent a further aspect of the invention.

DETAILED DESCRIPTION OF THE INVENTION

The benefits of the process of the present invention are, inter alia, the following: (a) compound [5] ($C^1=C^2$) may be isolated from a mixture containing also the undesirable isomer [6] by crystallization, (b) the undesirable isomer [6a] may be oxidized to give the starting compound [4] and (c) the highly selective reduction of the lactone-group of the compound [5] with diisobutylaluminum hydride may proceed at industrially acceptable temperature range from −50 to +50° C., preferably from −20 to +20° C.

The process of the present invention for the synthesis of 17-phenyl-18,19,20-trinor-PGF$_{2\alpha}$ and its derivatives of formula [1b] ($R^3$=$R^4$=H) may be summarized by the following Scheme 2.

Scheme 2
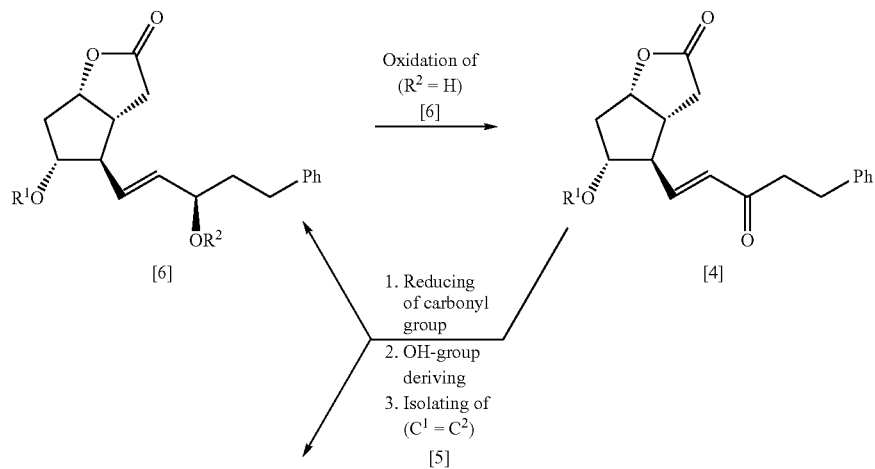
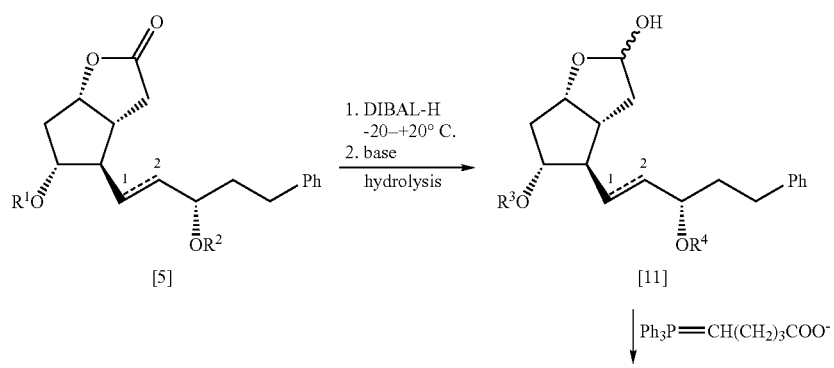
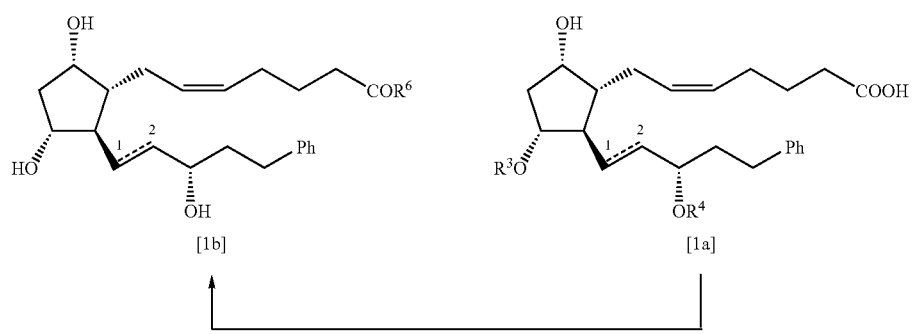

An alternative approach to prepare compound [5] may involve separating by column chromatography the compound [5a] from [6a], formed after reducing the ketone [4] and oxidizing the hydroxyl group of the compound [6a] for regeneration of the compound [4] and deriving the hydroxyl groups of the compound [5a] to yield the compound [5] (Scheme 3):

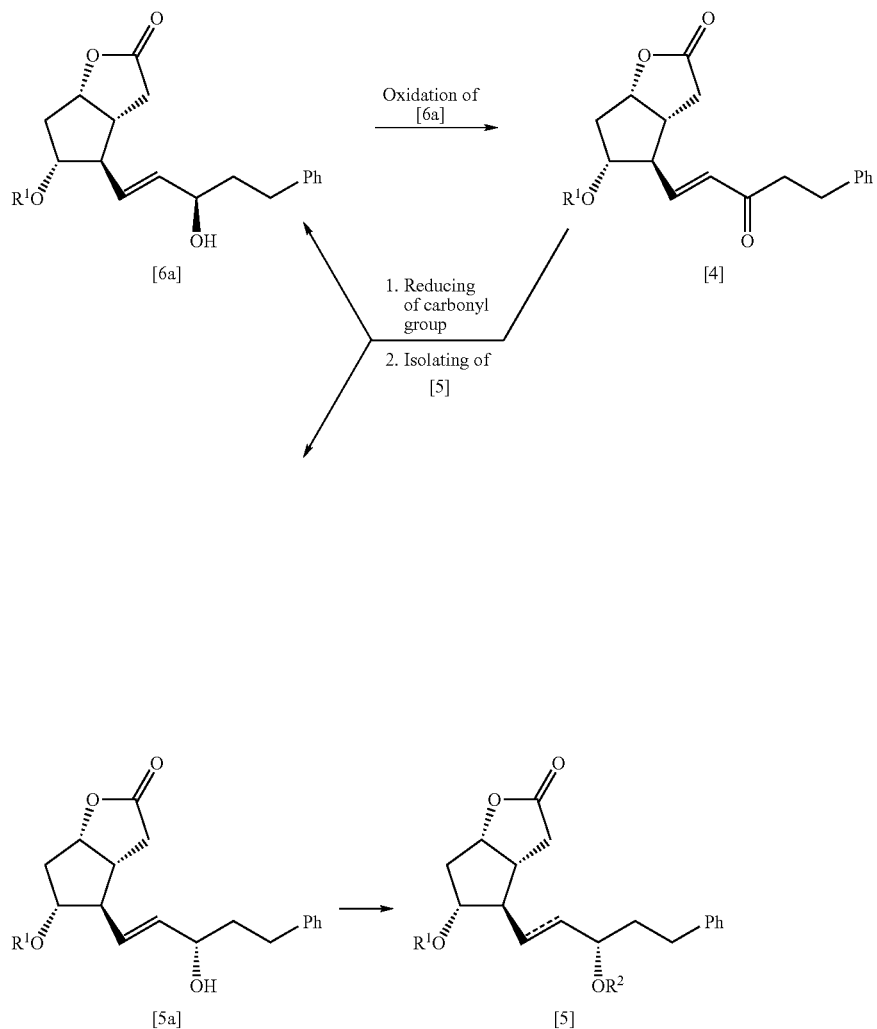

Preferably the $R^1$ and $R^2$ are selected from the group consisting of benzoyl, p-toluoyl, p-phenylbenzoyl and tetrahydro-2H-pyran-2-yl groups.

Preferably the stereoselective reduction of the compound [4] is carried out with (−)-B-chlorodiisopinocamphenylborane or with borane in the presence of 2-alkyl-CBS-oxazaborolydines. More preferably the reduction is carried out with (−)-B-chlorodiisopinocamphenylborane in organic solvent. Preferably the organic solvent is tetrahydrofuran, ether, 1,2-dimethoxyethane, toluene, hexane, dichloromethane or mixtures of these solvents.

Preferably the catalyst for hydrogenation of compound [5] ($C^1$=$C^2$) to compound [5] ($C^1$—$C^2$) contains palladium, platinum or nickel. More preferably the catalyst is palladium-on-carbon, platinum oxide or platinum-on-carbon. Preferably the hydrogenation is carried out in the presence of solvents and bases or salts. Preferably the bases are selected from the group consisting of tertiary and secondary amines. Preferably the salts are selected from the group consisting of metal nitrites, metal alkanoates and metal benzoates.

An important benefit of the process of the present invention is that some of the new compounds of the formula [5] may be purified by crystallization from organic solvents.

When the reduction of the compound [5] is carried out with about 2 equivalents of diisobutylaluminum hydride (DIBAL-H), an intermediate [10] may be isolated from the reaction mixture. Basic hydrolysis of the compound [10] gives the compound [11]. However, it should be noted that using excess of diisobutylaluminum hydride (DIBAL-H) for reduction of compound [5] to compound [11] at −50–+50° C. is complicated by further reduction to by-product [12]:

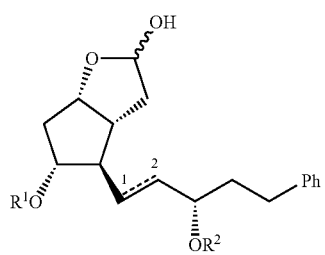

[10]

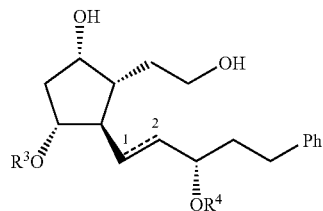

[12]

wherein $R^1$, $R^2$, $R^3$ and $R^4$ are as defined above and the bond between carbons 1–2 is either a single or a double carbon-carbon bond.

To increase the yield of [11] it is desirable to add DIBAL-H to compound [5] at −50–+50° C. (preferably at −20–+20° C.) to attain about 95–99% conversion of lactone-groups. Preferably, this reaction is conducted in the presence of an organic solvent. Preferably, the organic solvent is toluene, tetrahydrofuran, ether, dichloromethane or mixture thereof. Preferably, the following basic hydrolysis is conducted with organic bases or metal hydroxides or carbonates in a solvent possibly in the presence of phase transfer catalyst. Preferably the metal is alkali or alkaline-earth metal and the solvent is a neutral organic solvent, $C_{1-4}$ alkanol or water or mixture thereof. The process of reduction of the compound [5] with diisobutylaluminum hydride may be presented by Scheme 4:

Scheme 4

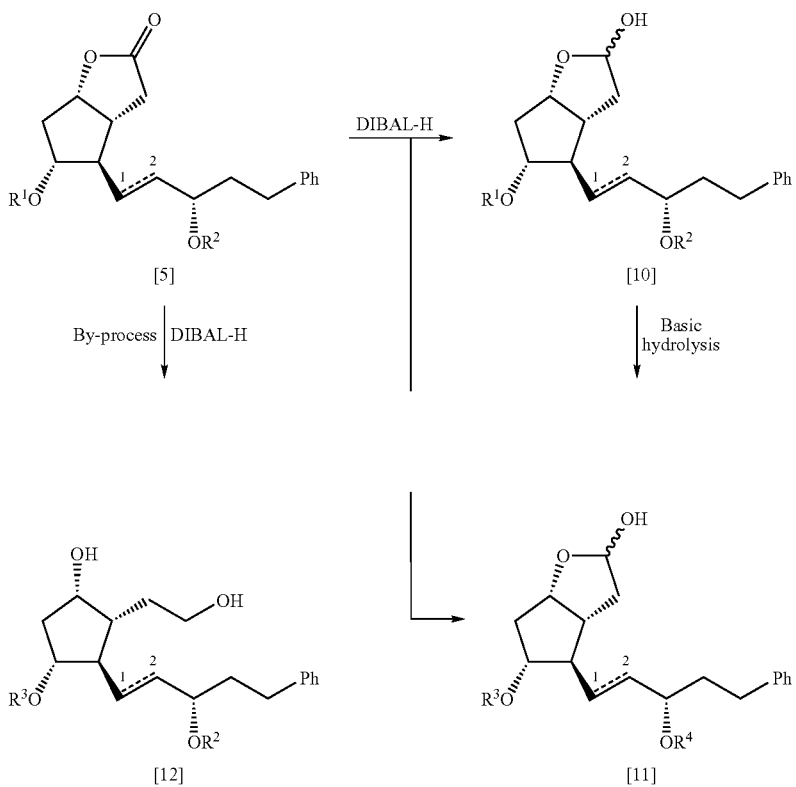

wherein $R^1$, $R^2$, $R^3$, and $R^4$ are as defined above and C1–C2 bond is single or double carbon-carbon bond.

It is desired to purify compounds [5], [11], 17-phenyl-18, 19,20-trinor-PGF$_{2\alpha}$ and its derivatives by column chromatography or/and crystallization of the compounds either per se or in the form of salts thereof with amines. Preferably the amines are tromethamine, histamine, L-arginine, triptamine or adamantanamine.

Esterification of the carboxylic groups of 17-phenyl-18, 19,20-trinor-PGF$_{2\alpha}$ and its derivatives is provided by reaction of the acids with alcohols or diazoalkane compounds, e.g. diazomethane. Preferably the esterification is carried out with alkyl iodide, bromide, methanesulfonate, p-toluenesulfonate, p-nitrophenylsulfonate, 2,4-dinitrophenylsulfonate or triflate in the presence of organic solvent and organic or inorganic base. Preferably the organic base is 1,8-diazabicyclo[5.4.0]undec-7-ene (DBU), N,N-diisopropylethylamine or diisopropylamine. Preferably the inorganic base is alkali or alkaline-earth metal carbonate or hydroxide. Most preferably, the inorganic base is potassium or cesium carbonate. Preferably the solvent is acetone, methyl ethyl ketone, THF, DMF, dichloromethane, ethanol, isopropanol or acetonitrile.

17-Phenyl-18,19,20-trinor-PGF$_{2\alpha}$N-alkylamide and its derivatives may be prepared by reacting 17-phenyl-18,19, 20-trinor-PGF$_{2\alpha}$ or its ester Preferably methyl ester) and its derivatives with an alkylamine according to standard procedures.

The compound [4] may be prepared from the commercially available compounds [2a–c] according to Scheme 5:

EXAMPLES

This invention will be better understood from the Examples that follow. However, the examples illustrate, but do not limit, the invention.

Example 1

(3aR,4R,5R,6aS)-Hexahydro-4-(3-oxo-5-phenyl-1E-pentenyl)-5-(p-phenylbenzoyl oxy)-2H-cyclopenta[b]furan-2-one [4a]

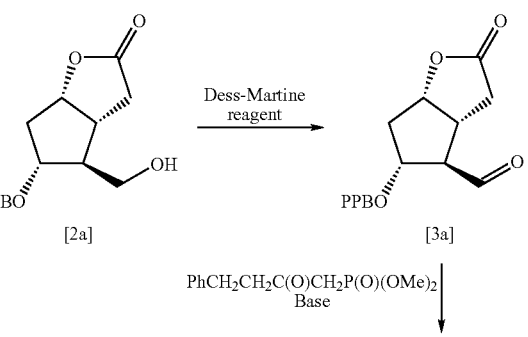

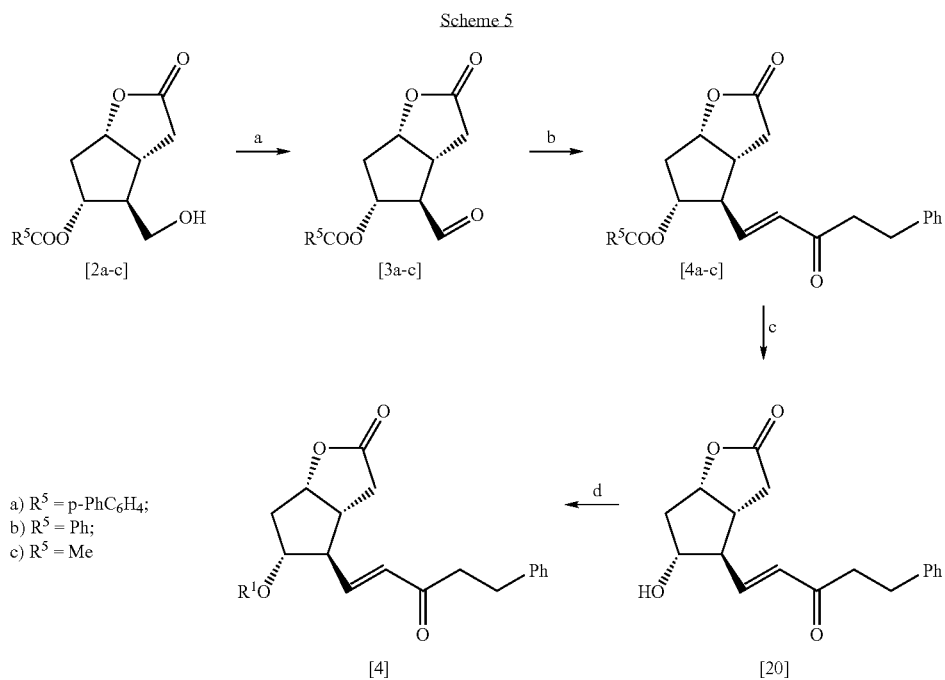

where R$^1$ is defined above.
Reagents:
(a) Dess-Martin reagent;
(b) PhCH$_2$CH$_2$COCH$_2$PO(OMe)$_2$ and Base or PhCH$_2$CH$_2$COCH=PPh$_3$;
(c) basic hydrolysis;
(d) Derivation of OH-group.

-continued

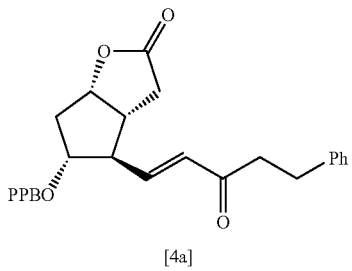

[4a]

wherein PPB is p-phenylbenzoyl group.

1) Preparation of dimethyl (2-oxo-4-phenylbutyl)phosphonate 1.1) 1-Bromo-4-phenyl-2-butanone A freshly prepared solution of bromine (258.9 g) in methanol (600 mL) was added dropwise during 1 h 20 min to a stirred solution of benzylacetone (222.3 g) in methanol (600 mL) at 7–10° C. An exothermic reaction took place, and to maintain the necessary temperature (7–10° C.), the flask should be immersed in a ice-water bath. When orange-red color of bromine disappeared, water (1500 mL) was added to the mixture and the obtained mixture was stirred overnight. The organic layer (on the bottom) was separated, water phase was extracted with dichloromethane (2×600 mL). The combined organic layers were dried over sodium sulfate, filtered and evaporated under reduced pressure. The oily residue was dissolved in hexane (2500 mL) and the obtained solution was kept overnight at −10° C. Precipitated fine crystals (needles) were filtered off, washed on filter with cold hexane, dried under reduced pressure at room temperature to give 1-bromo-4-phenyl-2-butanone (213.0 g, 63% yield), mp 39–40° C. $^1$H NMR (CDCl$_3$) δ 2.95–3.00 (m, 4H); 3.83 (s, 2H); 7.16–7.30 (m, 5H).

1.2) 1-Iodo-4-phenyl-2-butanone

A solution of 1-bromo-4-phenyl-2-butanone (18.9 g) in dry acetone (100 mL) was added dropwise to a stirred solution of sodium iodide (14.0 g) in dry acetone (100 mL) at room temperature. A precipitate of sodium bromide immediately formed. The mixture was stirred overnight at room temperature, filtered and evaporated under reduced pressure. The residue was dissolved in dichloromethane (150 mL). The solution was washed with water, dried over sodium sulfate and evaporated under reduced pressure. The oily residue was dissolved in 95% ethanol (100 mL). The obtained solution was kept at −10° C. overnight. Precipitated pale yellow needles were filtered off, dried under reduced pressure at room temperature to obtain 20.0 g (88% yield) of 1-iodo-4-phenyl-2-butanone, mp 44–45° C. $^1$H NMR (CDCl$_3$) δ: 2.88–3.07 (m, 4H); 3.75 (s, 2H); 7.16–7.31 (m, 5H).

1.3) Dimethyl (2-oxo-4-phenylbutyl)phosphonate

A 0.5 L four necked flask equipped with condenser connected to bubbler, thermometer, dropping funnel with pressure equalization arm and deep-tube for bubbling argon through the reaction mixture was charged with a solution of 1-iodo-4-phenyl-2-butanone (89.5 g) in acetonitrile (250 mL). Trimethylphosphite (80.9 g) was added dropwise to the solution, over 1.5 h, with simultaneous bubbling of an argon through the reaction mixture. The temperature of the reaction mixture was allowed to change from 23° C. to 43° C. The resulting mixture was refluxed during 1 h and evaporated under reduced pressure. The residue was fractionally distilled at 0.05 mm Hg to give 71.0 g (85% yield) of dimethyl (2-oxo-4-phenylbutyl)phosphonate, bp 129–130° C./0.05 mm Hg. $^1$H NMR (CDCl$_3$, δ) 2.88–2.92 (m, 4H); 2.98 (t, J=23 Hz; 2H); 3.68 (s, 3H); 3.74 (s, 3H); 7.14–7.24 (m, 5H).

2) Preparation of (3aR,4R,5R,6aS)-4-formylhexahydro-5-p-phenylbenzoyloxy)-2H-cyclopenta[b]furan-2-one [3a]

Corey lactone [2a] (80.7 g) was added by portions to a stirred suspension of Dess-Martine reagent (116.6 g) in dichloromethane (700 mL) at 0–3° C. (ice/water bath). The mixture was stirred for 40 min (temperature rose to 14° C.) until lactone [2a] spot disappeared in TLC monitoring. The resulting mixture poured into a solution of sodium bicarbonate (130 g) and sodium thiosulfate pentahydrate (350 g) in water (1.5 L). The mixture was stirred for about 10 min. The organic layer was separated and the water layer was extracted with dichloromethane (2×350 mL). The combined organic solutions were washed with saturated solution of sodium bicarbonate, dried over sodium sulfate, filtered and immediately introduced into the following step.

3) Preparation of (3aR,4R,5R,6aS)-hexahydro-4-(3-oxo-5-phenyl-1E-pentenyl)-5-(p-phenylbenzoyloxy)-2H-cyclopenta[b]furan-2-one [4a]

A solution of dimethyl (2-oxo-4-phenylbutyl)phosphonate (69.1 g) in dichloromethane (200 mL) was added dropwise at 0° C. to a suspension of sodium hydride (11.9 g) in dichloromethane (700 mL). The mixture was stirred at 0° C. during 1 h. The cold (0–5° C.) solution of aldehyde [3a] in dichloromethane prepared in the previous stage was added dropwise to the stirred mixture at 0–5° C. The obtained mixture was stirred for 1 hour at the same temperature (TLC monitoring), filtered through Celite and acidified with acetic acid to pH 5 at 0–5° C. The organic layer was separated, washed with water until the pH of the water layer was not less than 6.8, dried over sodium sulfate, filtered and evaporated under reduced pressure. The oily residue was triturated with ether (500 mL). The precipitated crystals were filtered and dried under reduced pressure to a constant weight to give 93.4 g (85% yield) of crude crystalline product. A solution of the product in acetonitrile was passed through Celite and evaporated under reduced pressure. The crystalline residue was recrystallized from methanol (2 L) gave 83.6 g (76.2% yield) of compound [4a] with mp 134–135° C. and $[\alpha]_D^{20}$ −141.7° (c 1.26, MeCN). $^1$H NMR (CDCl$_3$, δ) 2.32–2.63 (m, 3H); 2.84–2.97 (m, 7H); 5.00–5.10 (m, 1H); 5.20–5.35 (m, 1H); 6.20 (d, J=16 Hz, 1H); 6.65 (dd, J=16 and 8 Hz, 1H); 7.15–7.67 (m, 12H); 8.03 (d, J=8 Hz, 2H).

Example 2

(3aR,4R,5R,6aS)-Hexahydro-5-(p-phenylbenzoyloxy)-4-[(3S)-5-phenyl-3-[(tetrahydro-2H-pyran-2-yl)oxy]-1E-pentenyl]-2H-cyclopenta[b]furan-2-one [5] (C¹═C², R¹=PPB and R²=THP)

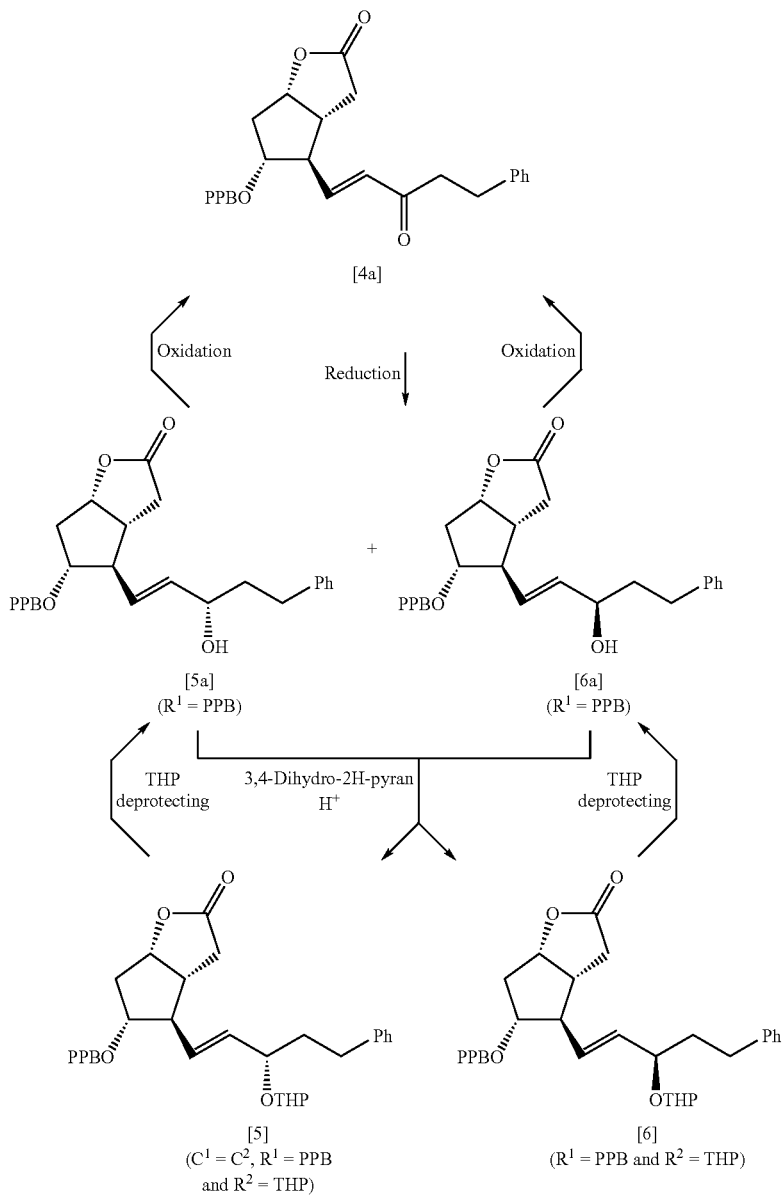

1) Preparation of (3aR,4R,5R,6aS)-hexahydro-4-[(3S) and (3R)-3-hydroxy-5-phenyl-1E-pentenyl]-5-p-phenylbenzoyloxy)-2H-cyclopenta[b]furan-2-ones [5a] (R¹=PPB) and [6a] (R¹=PPB)

A solution of (−)-B-chlorodiisopinocamphenylborane (26.0 g) in THF (150 mL) was added dropwise at −23−−25° C. to a stirred solution of the compound [4a] (26.0 g) in THF (250 mL). The mixture was stirred at this temperature during 8 h (TLC monitoring) and then quenched by adding 30 mL of Methanol at −23−−25° C. The resulting solution was allowed to warm to room temperature and was stirred at this temperature for 14 h. The mixture was concentrated to a volume 70–100 mL and dichloromethane (400 mL) and water (200 mL) were added to it. The organic layer was separated, water layer was extracted with dichloromethane (3×100 mL). The combined organic layers were washed with a 25 wt. % aq. solution of ammonium chloride (2×80 g), dried over sodium sulfate, filtered and evaporated under reduced pressure. The residue {[5a] (R¹=PPB)/[6a] (R¹=PPB) 95:5 by HPLC} was triturated with hexane (150 mL) and the obtained solid was filtered off. This solid with methanol (20 mL) and isopropyl ether (130 mL) was refluxed during 30 min and cooled to room temperature. The precipitated solid was filtered off and dried under reduced pressure to give 22.0 g (85% yield) of a mixture of compounds [5a] ($R^1$=PPB) and [6a] ($R^1$=PPB), where [5a] ($R^1$=PPB)/[6a] ($R^1$=PPB) is 96:4 by HPLC.

2) Preparation of (3aR,4R,5R,6aS)-hexahydro-5-(p-phenylbenzoyloxy)-4-[(3S)-5-phenyl-3-[(tetrahydro-2H-pyran-2-yl)oxy]-1E-pentenyl]-2H-cyclopenta[b]furan-2-one [5] ($C^1$=$C^2$, $R^1$=PPB and $R^2$=THP) and its (3R)-isomer [6] ($R^1$=PPB and $R^2$=THP)

Pyridinium p-toluenesulfonate (0.2 g) was added to a stirred solution of diastereomeric alcohols [5a] ($R^1$=PPB) and [6a] ($R^1$=PPB) {23.8 g, [5a] ($R^1$=PPB)/[6a] ($R^1$=PPB) 96:4 by HPLC}, and 3,4-dihydro-2H-pyran (15.7 g) in dichloromethane (250 mL) at room temperature. The mixture was stirred overnight at room temperature (TLC monitoring), washed with saturated aqueous solution of sodium bicarbonate and brine, dried over sodium sulfate, filtered and evaporated under reduced pressure. The residue was crystallized from methanol to give 19.9 g (71.1% yield) the compound [5] ($C^1$=$C^2$, $R^1$=PPB and $R^2$=THP). Analytical probe of the compound [5] ($C^1$=$C^2$, $R^1$=PPB and $R^2$=THP) may be prepared by repeated crystallization from mixture of hexane and ethyl acetate gave the compound [5] ($C^1$=$C^2$, $R^1$=PPB and $R^2$=THP) with mp 118–119° C. and $[\alpha]_D^{20}$ −91.2° (c 1, MeCN). $^1$H NMR (CDCl$_3$) δ: 7.96 (d, J=8 Hz, 2H); 7.50–7.56 (m, 4H); 7.29–7.40 (m, 3H); 7.01–7.17 (m, 5H); 5.38–5.61 (m, 2H); 5.15–5.18 (m, 1H); 4.95–5.00 (m, 1H); 4.42–4.53 (m, 1H); 3.95–4.05 (m, 1H); 3.55–3.80 (m, 1H); 3.15–3.40 (m, 1H). $^{13}$C (CDCl$_3$) δ: 19.4; 19.6; 25.3; 25.4; 30.7; 30.8; 31.2; 31.8; 34.5; 34.8; 36.3; 37.2; 37.4; 37.6; 42.4; 42.5; 53.8; 62.3; 62.4; 74.8; 78.6; 79.0; 82.8; 83.2; 94.9; 98.0; 125.7; 127.0; 127.1; 128.0; 128.1; 128.2; 128.6; 128.8; 130.0; 131.3; 133.7; 134.6; 139.8; 141.7; 145.9; 146.0; 165.7; 176.0; 176.2. IR (KBr): 2933; 1762; 1716; 1670; 1640; 1268 cm$^{-1}$.

The mother liquor which contains a mixture of the compounds [5] (C=$C^2$, $R^1$=PPB and $R^2$=THP) and [6] ($R^1$=PPB and $R^2$=THP) was evaporated under reduced pressure and subjected separation by column chromatography on Silica gel (elution with ethyl acetate/hexane 1:2 v/v) to afford additional 2.0 g (8.4%) of compound [5] ($C^1$=$C^2$, $R^1$=PPB and $R^2$=THP) and 0.9 g (3.8%) of isomer [6] ($R^1$=PPB and $R^2$=THP) with mp 116–118° C. and $[\alpha]_D^{20}$ −84.30 (c 1, MeCN). $^1$H NMR (CDCl$_3$) δ: 7.06–8.04 (m, 14H); 5.40–5.67 (m, 2H); 5.22–5.39 (m, 1H); 5.00–5.15 (m, 1H); 4.61 (m, 1H); 4.02–4.17 (m, 1H); 3.78–3.87 (m, 1H); 3.30–3.50 (m, 1H); 2.45–2.93 (m, 7H); 2.18–2.28 (m, 1H); 1.53–2.03 (m, 8H).

3) Preparation of (3aR,4R,5R,6aS)-hexahydro-4-[(3R)-3-hydroxy-5-phenyl-1E-pentenyl]-5-p-phenylbenzoyloxy)-2H-cyclopenta[b]furan-2-one [6a] ($R^1$=PPB)

Pyridinium p-toluenesulfonate (20 mg) was added to a stirred solution of the compound [6] ($R^1$=PPB and $R^2$=THP) (0.44 g), obtained in previous step, in methanol (20 mL) at room temperature. The mixture was stirred at 40–50° C. for 3–4 hours (TLC monitoring) and evaporated under reduced pressure. The residue was diluted with dichloromethane (30 mL). The solution was washed with saturated aqueous solution of sodium bicarbonate (10 mL) and brine (10 mL), dried over sodium sulfate, filtered and evaporated to give 0.35 g (93.4%) of oily residue. The residue was crystallized from a mixture of hexane and ether to give compound [6a] ($R^1$=PPB) as white crystals with mp 81–83° C. and $[\alpha]_D^{20}$ −124.5° (c 1, MeCN). $^1$H NMR (CDCl$_3$) δ: 7.08–8.05 (m, 14H); 5.51–5.74 (m, 2H); 5.21–5.30 (m, 1H); 5.02–5.07 (m, 1H); 4.09–4.13 (m, 1H); 2.46–2.92 (m, 7H); 2.18–2.28 (m, 1H); 1.66–1.86 (m, 3H). $^{13}$C (CDCl$_3$) δ: 31.6; 34.8; 37.6; 38.7; 42.7; 54.1; 71.6; 79.0; 83.1; 125.9; 127.1; 127.2; 128.2; 128.3; 128.8; 128.9; 130.1; 136.2; 139.9; 141.5; 146.1; 165.9; 176.2.

4) Preparation of (3aR,4R,5R,6aS)-hexahydro-4-[(3S)-3-hydroxy-5-phenyl-1E-pentenyl]-5-(p-phenylbenzoyloxy)-2H-cyclopenta[b]furan-2-one [5a] ($R^1$=PPB)

Pyridinium p-toluenesulfonate (50 mg) was added to a stirred solution of the compound [5] ($C^1$=$C^2$, $R^1$=PPB and $R^2$=THP) (1.00 g) in methanol (50 mL) at room temperature. The mixture was stirred at 40–50° C. for 3–4 hours (TLC monitoring) and evaporated under reduced pressure. The residue was diluted with dichloromethane (75 mL). The solution was washed with saturated aqueous solution of sodium bicarbonate (25 mL) and brine (25 mL), dried over sodium sulfate, filtered and evaporated to give 0.69 g (81.0%) of oily residue. The residue was crystallized from a mixture of ethyl acetate and isopropyl ether to give compound [5a] ($R^1$=PPB) as white crystals with mp 126–128° C. $^1$H NMR (CDCl$_3$) is in agreement with the structure.

4) Regeneration of (3aR,4R,5R,6aS)-hexahydro-4-(3-oxo-5-phenyl-1E-pentenyl)-5-p-phenyl-benzoyloxy)-2H-cyclopenta[b]furan-2-one [4a]

4.1) From Compound [6a] ($R^1$=PPB)

A solution of pyridine sulfur trioxide (0.32 g) in DMSO (3.5 mL) was added dropwise to a stirred solution of compound [6a] ($R^1$=PPB) (0.30 g) and triethylamine (0.40 g) in dichloromethane (4 mL) at −5–0° C. The mixture was stirred at the same temperature for 1 hour (TLC monitoring) and poured into cold water (15 mL). The mixture was stirred for 10 min at 0–5° C. The organic layer was separated, the water layer was extracted with dichloromethane (3×5 mL). The combined organic layers were washed with brine (3×10 mL), dried over sodium sulfate, filtered and evaporated under reduced pressure. A solution of the residue in methanol (1 mL) was cold to −10° C. and kept at the same temperature for 3 hours. The precipitated crystals were filtered, washed on filter with cold methanol (2×1 mL) and dried under reduced pressure to a constant weight to give 0.26 g (87% yield) of crystalline compound [4a] with 94% purity by HPLC.

4.2) From Compound [5a] ($R^1$=PPB)

A solution of pyridine sulfur trioxide (0.60 g) in DMSO (7.0 mL) was added dropwise to a stirred solution of compound [5a] ($R^1$=PPB) (0.60 g) and triethylamine (0.80 g) in dichloromethane (8 mL) at −5–0° C. The mixture was stirred at the same temperature for 1 hour (TLC monitoring) and poured into cold water (30 mL). The mixture was stirred for 10 min at 0–5° C. The organic layer was separated, the water layer was extracted with dichloromethane (3×10 mL). The combined organic layers were washed with brine (3×20 mL), dried over sodium sulfate, filtered and evaporated under reduced pressure. A solution of the residue in methanol (2 mL) was cold to −10° C. and kept at the same temperature for 3 hours. The precipitated crystals were filtered, washed on filter with cold methanol (2×2 mL) and dried under reduced pressure to a constant weight to give 0.50 g (83.7% yield) of crystalline compound [4a].

Example 3

(3aR,4R,5R,6aS)-Hexahydro-5-(p-phenylbenzoy-loxy)-4-[(3R)-5-phenyl-3-[(tetrahydro-2H-pyran-2-yl)oxy]pentyl]-2H-cyclopenta[b]furan-2-one [5]
($C^1$—$C^2$, $R^1$=PPB and $R^2$=THP)

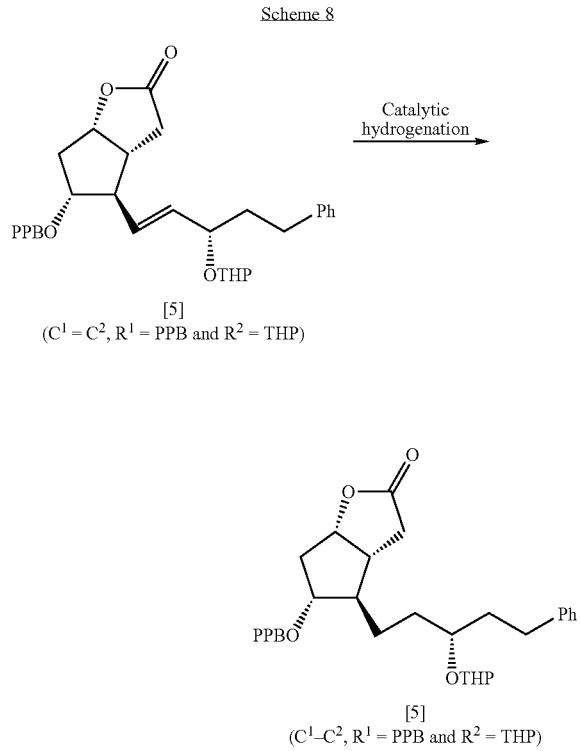

wherein PPB is p-phenylbenzoyl group and THP is tetrahydo-2H-pyran-2-yl group.

A mixture of a compound [5] ($C^1$═$C^2$, $R^1$=PPB and $R^2$=THP) (80.0 g), palladium on carbon catalyst (16 g) and ethyl acetate (1.0 L) was stirred under hydrogen atmosphere at 150 psi for 3 hours at room temperature. The reaction mixture was then filtered and evaporated under reduced pressure. The oily residue was crystallized from a mixture of hexane and ethyl acetate 4:1 v/v to give 71.4 g (89% yield) of compound [5] ($C^1$—$C^2$, $R^1$=PPB and $R^2$=THP), mp 103–105° C., $[\alpha]_D^{20}$ −107° (c 1.0, MeCN). $^1$H NMR (CDCl$_3$) δ: 8.03 (d, J=8 Hz, 2H); 7.60–7.67 (m, 4H); 7.36–7.48 (m, 3H); 7.14–7.24 (m, 5H); 5.20–5.30 (m, 1H); 5.00–5.15 (m, 1H); 4.50–4.70 (m, 1H); 3.89–3.95 (m, 1H); 3.66–3.72 (m, 1H); 3.45–3.50 (m, 1H). $^{13}$C NMR (CDCl$_3$) δ: 20.1; 25.4; 28.7; 31.3; 31.9; 36.5; 43.5; 52.8; 63.0; 76.0; 80.1; 84.3; 97.8; 125.7; 127.1; 127.2; 128.1; 128.3; 128.4; 128.9; 130.1; 140.0; 142.4; 146.0; 165.8; 176.7. IR (KBr): 2990; 1771; 1707; 1608; 1277; 1181; 1110; 1026; 751; 698 cm$^{-1}$.

Example 4

(3aR,4R,5R,6aS)-Hexahydro-5-(p-phenylbenzoy-loxy)-4-[(3S)-5-phenyl-3-[(tetrahydro-2H-pyran-2-yl)oxy]pentyl]-2H-cyclopenta[b]furan-2-one [22]

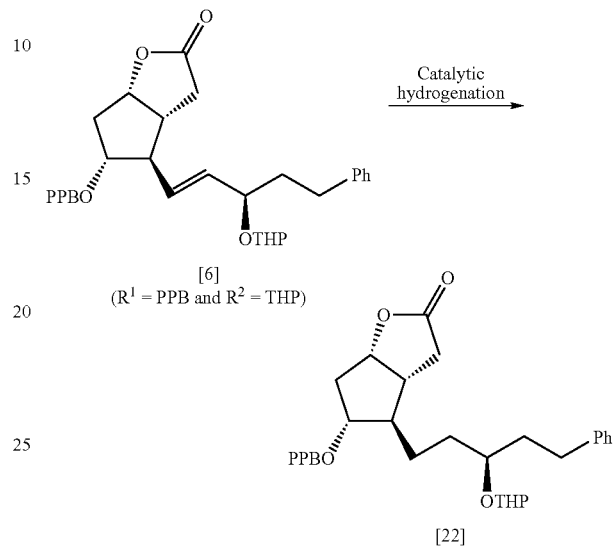

wherein PPB is p-phenylbenzoyl group and THP is tetrahydo-2H-pyran-2-yl group.

A mixture of a compound [6] ($R^1$=PPB and $R^2$=THP) (1.4 g), palladium on carbon catalyst (0.56 g) and ethyl acetate (40 mL) was stirred under hydrogen atmosphere at 40 psi for 3 hours at room temperature. The reaction mixture was then filtered and evaporated under reduced pressure. The oily residue was purified by column chromatography on silica gel elution with mixture of hexane and ethyl acetate 2:1 v/v to give 1.2 g (86% yield) of compound [22] as oil, $[\alpha]_D^{20}$ −52.3° (c 1.0, MeCN). $^1$H NMR (CDCl$_3$) δ: 1.41–1.86 (m, 12H); 2.00–2.25 (m, 1H); 2.34–3.00 (m, 7H); 3.40–3.60 (m, 1H); 3.60–3.80 (m, 1H); 3.80–4.00 (m, 1H); 5.00–5.15 (m, 1H); 4.50–4.70 (m, 1H); 3.89–3.95 (m, 1H); 3.66–3.72 (m, 1H); 3.45–3.50 (m, 1H).

Example 5

(3aR,4R,5R,6aS)-Hexahydro-5-(p-phenylbenzoy-loxy)-4-[(3R)-5-phenyl-3-[(tetrahydro-2H-pyran-2-yl)oxy]pentyl]-2H-cyclopenta[b]furan-2-one [5]
($C_1$—$C^2$, $R^1$=PPB and $R^2$=THP)

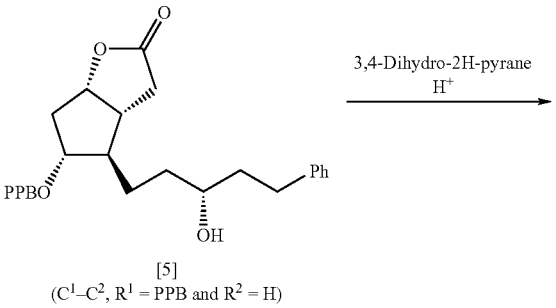

-continued

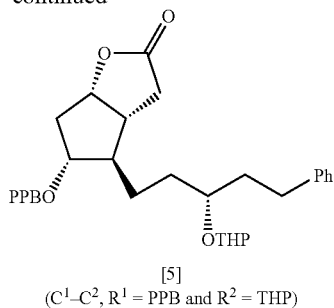

[5]
(C¹–C², R¹ = PPB and R² = THP)

wherein PPB is p-phenylbenzoyl group and THP is tetrahydro-2H-pyran-2-yl group.

Pyridinium p-toluenesulfonate (20 mg) was added to a stirred solution of compound [5] (C¹—C², R¹=PPB and R²=H) (2.4 g) and 3,4-Dihydro-2H-pyran (1.6 g) in dichloromethane (25 mL) at room temperature. The mixture was stirred overnight at room temperature (TLC monitoring), washed with saturated aqueous solution of sodium bicarbonate and brine, dried over sodium sulfate, filtered and evaporated under reduced pressure. The residue was crystallized from ether and recrystallized from mixture of hexane and ethyl acetate to give 2.31 g (82% yield) the compound [5] (C¹—C², R¹=PPB and R²=THP), mp 103–105° C. $^1$H NMR (CDCl$_3$) agrees with the structure Example 6

(3aR,4R,5R,6aS)-Hexahydro-5-(p-phenylbenzoyloxy)-4-[(3R)-5-phenyl-3-[(tetrahydro-2H-pyran-2-yl)oxy]pentyl]-2H-cyclopenta[b]furan-2-ol [11] (C¹—C², R³=PPB and R⁴=THP)

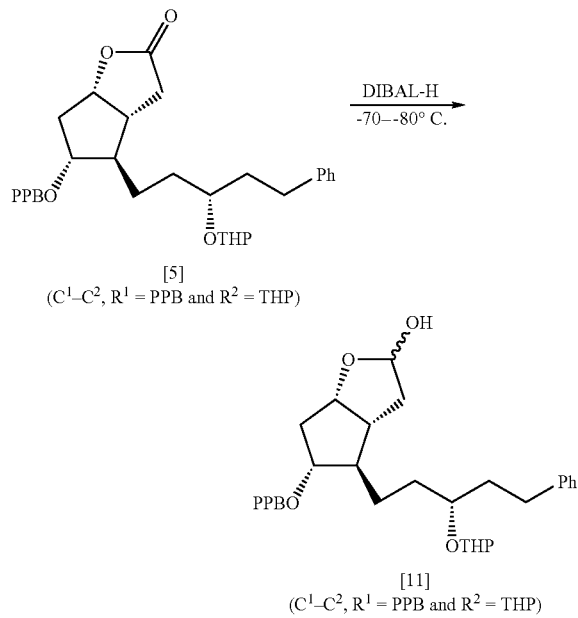

wherein PPB is p-phenylbenzoyl group and THP is tetrahydro-2H-pyran-2-yl group.

A 1.5 M solution of diisobutylaluminum hydride in toluene (6.0 mL, 9.0 mmol) was added dropwise to a stirred solution of compound [5] (C¹—C², R³=PPB and R⁴=THP) (4.1 g, 7.2 mmol) in toluene (60 mL) at −70—−80° C. (acetone/dry ice bath) and the resulting mixture was stirred during 1 h at the same temperature. Methanol (10 mL) was added dropwise to the stirred mixture at −70—−80° C. The mixture was stirred for 1 hour at room temperature, filtered and evaporated under reduced pressure. Dichloromethane (30 mL) was added to the residue. The resulting solution was washed with brine (2×10 mL), dried over sodium sulfate, filtered and evaporated under reduced pressure. The residue was purified by column chromatography on silica gel (hexane/ethyl acetate 2:1 v/v) to obtain 2.0 g (49% yield) of the compound [11] (C¹—C², R³=PPB and R⁴=THP). $^1$H NMR (CDCl$_3$) δ: 6.4–6.5 (m, 1H); 5.0–5.2 (m, 1H); 4.7–4.9 (m, 1H); 4.5–4.7 (m, 1H); 3.8–4.0 (m, 1H); 3.6–3.8 (m, 1H); 3.4–3.6 (m, 1H). $^{13}$C NMR (CDCl$_3$) δ: 20.1; 25.5; 28.6; 31.3; 31.6; 36.7; 37.7; 40.3; 41.1; 46.2; 51.6; 63.0; 81.3; 82.0; 97.8; 100.2; 125.6; 127.1; 127.2; 128.1; 128.3; 128.4; 128.9; 129.2; 130.0; 130.1; 140.0; 145.7; 166.0. IR (KBr): 3500, 2945, 1712, 1605, 1278, 1117, 1026, 752 cm$^{-1}$.

Example 7

(3aR,4R,5R,6aS)-Hexahydro-5-(p-phenylbenzoyloxy)-4-[(3S)-5-phenyl-3-[(tetrahydro-2H-pyran-2-yl)oxy]-1E-pentenyl]-2H-cyclopenta[b]furan-2-ol [11] (C¹=C², R³=PPB and R⁴=THP)

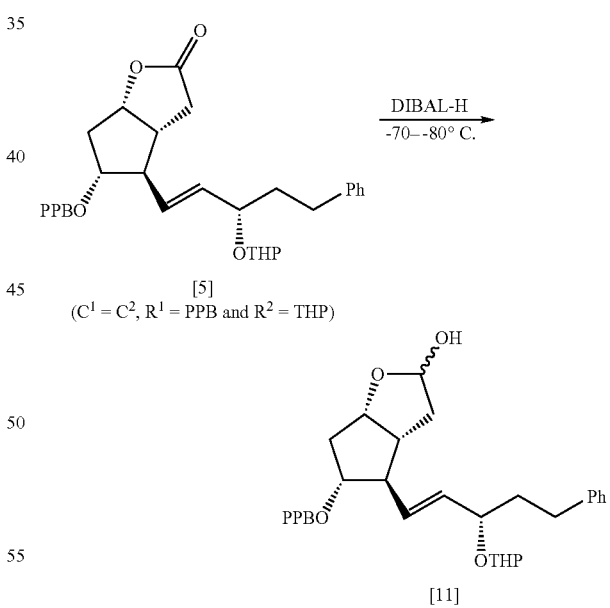

wherein PPB is p-phenylbenzoyl group and THP is tetrahydro-2H-pyran-2-yl group.

According to the method of Example 6 the compound [11] (C¹=C², R³=PPB and R⁴=THP) was obtained using compound [5] (C¹=C², R³=PPB and R⁴=THP) instead of compound [5] (C¹—C², R³=PPB and R⁴=THP).

The compound [11] (C¹=C², R³=PPB and R⁴=THP). $^1$H NMR (CDCl$_3$) δ: 7.0–8.1 (m, 14H); 5.4–5.8 (m, 3H);

5.0–5.3 (m, 1H); 4.0–4.2 (m, 1H); 3.6–3.9 (m, 1H); 3.2–3.5 (m, 2H); 2.5–3.0 (m, 5H); 1.2–2.1 (m, 13H).

Example 8

(3aR,4R,5R,6a)-Hexahydro-5-hydroxy-4-[(3R)-5-phenyl-3-[(tetrahydro-2H-pyran-2-yl)oxy]pentyl]-2H-cyclopenta[b]furan-2-ol [11] ($C^1$—$C^2$, $R^3$=H and $R^4$=THP)

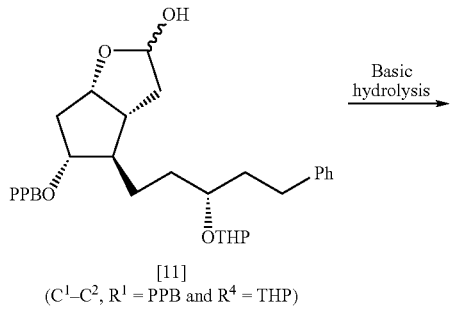

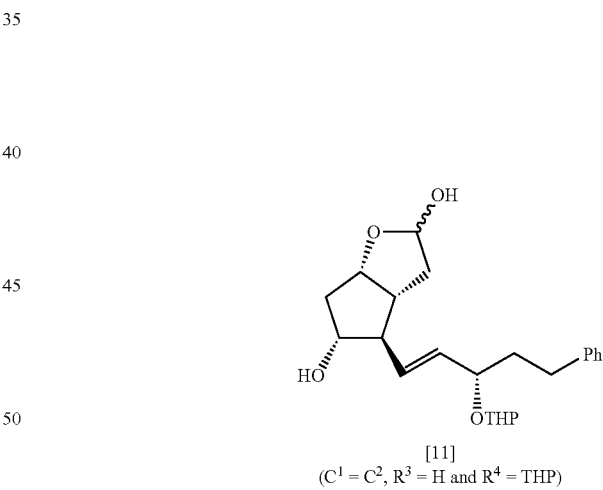

wherein PPB is p-phenylbenzoyl group and THP is tetrahydro-2H-pyran-2-yl group.

A mixture of compound [11] ($C^1$—$C^2$, $R^3$=PPB and $R^4$=THP) (2.0 g) and potassium carbonate (1.0 g) in methanol (10 mL) was stirred at 40–45° C. for 5 hours (TLC monitoring). Dichloromethane (20 mL) and water (20 mL) were added to the stirred mixture at room temperature. Organic layer was separated, washed with water, dried over sodium sulfate, filtered and evaporated under reduced pressure. The residue was purified by column chromatography on silica gel. The compound [11] ($C^1$—$C^2$, $R^3$=H and $R^4$=THP) (1.0 g, 73% yield) was prepared.

Example 9

(3aR,4R,5R,6aS)-Hexahydro-5-hydroxy-4-[(3S)-5-phenyl-3-[(tetrahydro-2H-pyran-2-yl)oxy]-1E-pentenyl]-2H-cyclopenta[b]furan-2-ol [11] ($C^1$=$C^2$, $R^3$=H and $R^4$=THP)

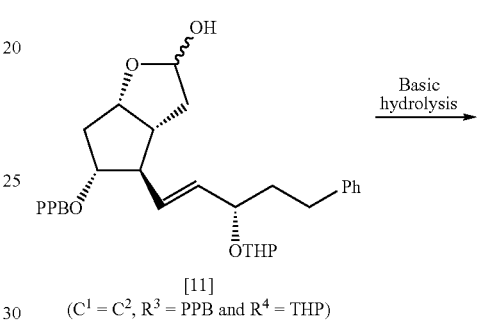

wherein PPB is p-phenylbenzoyl group and THP is tetrahydro-2H-pyran-2-yl group.

According to the method of Example 8 the compound [11] ($C^1$=$C^2$, $R^3$=H and $R^4$=THP) was obtained using compound [11] ($C^1$=$C^2$, $R^3$=PPB and $R^4$=THP) instead of compound [11] ($C^1$—$C^2$, $R^3$=PPB and $R^4$=THP).

Example 10

(3aR,4R,5R,6aS)-Hexahydro-5-hydroxy-4-[(3R)-5-phenyl-3-[(tetrahydro-2H-pyran-2-yl)oxy]pentyl]-2H-cyclopenta[b]furan-2-ol [11] ($C^1$—$C^2$, $R^3$=H and $R^4$=THP)

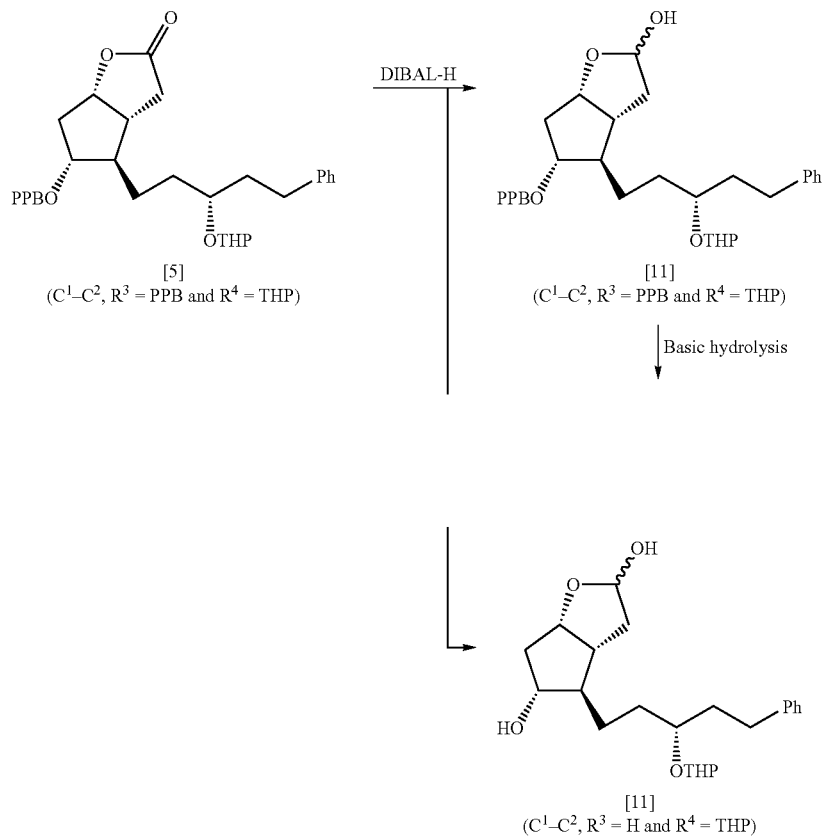

wherein PPB is p-phenylbenzoyl group and THP is tetrahydro-2H-pyran-2-yl group.

A 1.5 M solution of diisobutylaluminum hydride in toluene (46.0 mL, 69 mmol) was added dropwise to a stirred solution of compound [5] ($C^1$—$C^2$, $R^3$=PPB and $R^4$=THP) (17.0 g, 30 mmol) in toluene (500 mL) at −20—−10° C. The mixture was stirred for 1 hour at the same temperature. Methanol (200 mL) was added dropwise to the stirred mixture at −20—−10° C. The obtained mixture was stirred for 1 hour at room temperature, filtered and evaporated under reduced pressure. Dichloromethane (250 mL) was added to the residue. The resulting solution was washed with brine (2×220 mL), dried over sodium sulfate, filtered and evaporated under reduced pressure. To complete hydrolysis of p-phenylbenzoate-groups a mixture of the residue and potassium carbonate (10.0 g) in methanol (100 mL) was stirred at room temperature for 7 hours (TLC monitoring). The mixture was evaporated under reduced pressure. A mixture of the residue, dichloromethane (300 mL) and water (300 mL) was stirred for 10 min at room temperature. The organic layer was separated, washed with brine, dried over sodium sulfate, filtered and evaporated under reduced pressure. The residue was purified by column chromatography on silica gel (hexane/ethyl acetate 1:2 v/v) to obtain 10.3 g of the compound [11] ($C^1$—$C^2$, $R^3$=H and $R^4$=THP) (88% yield), $[\alpha]_D^{20}$ −53.5° (c 1.0, MeCN). $^1$H NMR (CDCl$_3$) δ: 7.10–7.29 (m, 5H); 5.47–5.63 (m, 1H); 4.57–4.69 (m, 2H); 3.69–3.94 (m, 2H); 3.60–3.75 (m, 1H); 3.40–3.55 (m, 1H). $^{13}$C NMR (CDCl$_3$) δ: 19.9; 25.4; 29.0; 31.2; 31.9; 36.6; 40.2; 41.5; 42.5; 46.4; 48.0; 55.3; 55.6; 62.8; 79.4; 79.9; 82.4; 86.4; 97.6; 100.0; 101.1; 125.6; 128.2; 128.3; 142.5. IR (neat): 3398, 2944, 2867, 1451 cm$^{-1}$.

Example 11

(3aR,4R,5R,6aS)-Hexahydro-5-hydroxy-4-[(3S)-5-phenyl-3-[(tetrahydro-2H-pyran-2-yl)oxy]-1E-pentenyl]-2H-cyclopenta[b]furan-2-ol [11] ($C^1=C^2$, $R^3$=H and $R^4$=THP)

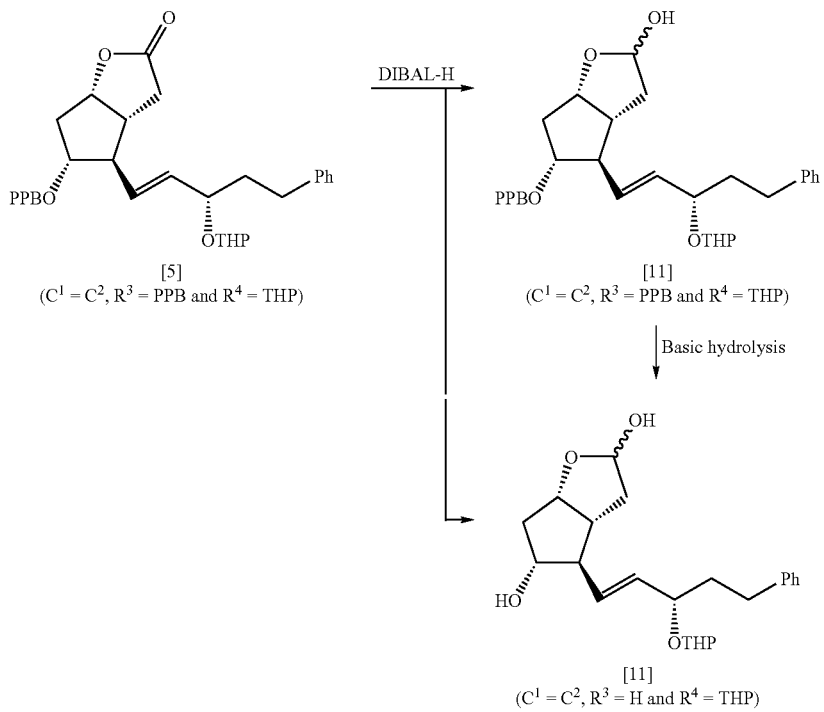

wherein PPB is p-phenylbenzoyl group and THP is tetrahydro-2H-pyran-2-yl group.

A 1.5 M solution of Diisobutylaluminum hydride in toluene (17.3 mL, 25.9 mmol) was added dropwise to a stirred solution of compound [5] ($C^1=C^2$, $R^3$=PPB and $R^4$=THP) (4.9 g, 8.6 mmol) in toluene (100 mL) at −20–−10° C. The mixture was stirred for 1 hour at the same temperature. Methanol (50 mL) was added dropwise to the stirred mixture at −20–−10° C. The obtained mixture was stirred for 1 hour at room temperature, filtered and evaporated under reduced pressure. Dichloromethane (100 mL) was added to the residue. The resulting solution was washed with brine (2×10 mL), dried over sodium sulfate, filtered and evaporated under reduced pressure. To complete hydrolysis of p-phenylbenzoate-groups a mixture of the residue and potassium carbonate (0.5 g) in methanol (50 mL) was stirred at room temperature for 7 hours (TLC monitoring). The mixture was evaporated under reduced pressure. A mixture of the residue, dichloromethane (100 mL) and water (50 mL) was stirred for 10 min at room temperature. The organic layer was separated, washed with brine, dried over sodium sulfate, filtered and evaporated under reduced pressure. The residue was purified by column chromatography on silica gel (hexane/ethyl acetate 1:2 v/v) to obtain 3.2 g of the compound [11] ($C^1=C^2$, $R^3$=H and $R^4$=THP) (95% yield). Crystallization the crude compound from ether give 2.3 g (68% yield) of the compound [11] ($C^1=C^2$, $R^3$=H and $R^4$=THP) as white crystals with mp 104.7–106.5° C. IR (KBr): 3396, 2942, 2883, 1602, 1497, 1453, 1330, 1129, 1075, 1039, 993, 904, 867, 810, 737, 696, 551 cm$^{-1}$.

Example 12

(3aR,4R,5R,6aS)-Hexahydro-5-hydroxy-4-[(3R)-5-phenyl-3-[(tetrahydro-2H-pyran-2-yl)oxy]pentyl]-2H-cyclopenta[b]furan-2-ol [11] ($C^1—C^2$, $R^3$=H and $R^4$=THP)

Scheme 17

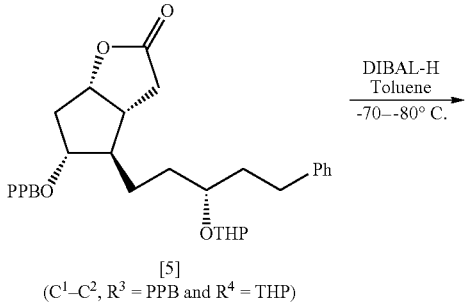

-continued

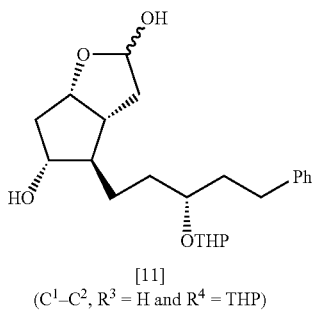

[11]
($C^1$—$C^2$, $R^3$ = H and $R^4$ = THP)

wherein PPB is p-phenylbenzoyl group and THP is tetrahydro-2H-pyran-2-yl group.

A 1.5 M solution of Diisobutylaluminum hydride in toluene (12.6 mL, 18.9 mmol) was added dropwise to a stirred solution of a compound [5] ($C^1$—$C^2$, $R^3$=PPB and $R^4$=THP) (4.1 g, 7.2 mmol) in toluene (60 mL) at −70–−80° C. (acetone/dry ice bath). The mixture was stirred for 1 hour at the same temperature. Methanol (50 mL) was added dropwise to the stirred mixture at −70–−80° C. and the cooling bath was removed. The mixture was stirred for 1 hours at room temperature, filtered and evaporated under reduced pressure. A solution of the residue in dichloromethane (150 mL) was washed with brine (2×10 mL), dried over sodium sulfate, filtered and evaporated under reduced pressure. The residue was purified by column chromatography on silica gel (hexane/ethyl acetate 1:2 v/v) to obtain compound [11] ($C^1$—$C^2$, $R^3$=H and $R^4$=THP) (2.53 g, 90% yield).

Example 13

(1R,2R,3R,5S)-3,5-dihydroxy-2-[(3R)-5-phenyl-3-[(tetrahydro-2H-pyran-2-yl)oxy]pentyl]cyclopentaneethanol [12a]

Scheme 18

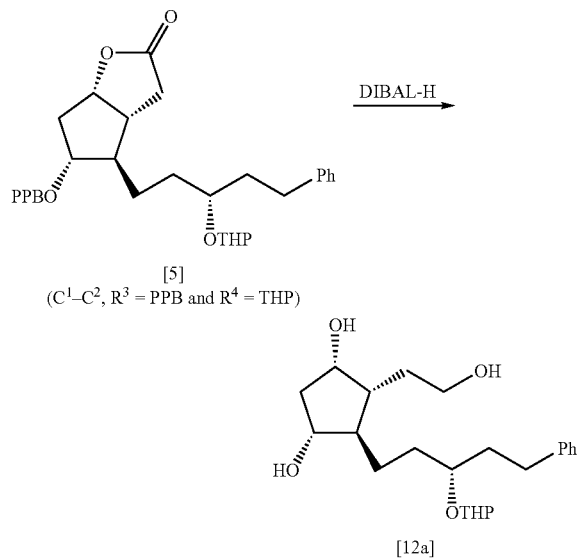

wherein PPB is p-phenylbenzoyl group and THP is tetrahydro-2H-pyran-2-yl group.

A 1.5 M solution of diisobutylaluminum hydride in toluene (12.6 mL, 18.9 mmol) was added dropwise to a stirred solution of a compound [11] ($C^1$—$C^2$, $R^3$=H and $R^4$=THP) (2.0 g, 3.5 mmol) in toluene (60 mL) at room temperature. The mixture was stirred for 3 hour at the same temperature. Methanol (50 mL) was added dropwise to the stirred mixture at −5–+5° C. and the cooling bath was removed. The mixture was stirred for 1 hours at room temperature, filtered and evaporated under reduced pressure. The residue was purified by column chromatography on silica gel (hexane/ethyl acetate 1:5 v/v) to obtain 1.0 g (73% yield) of the compound [12a]. $^1$H and $^{13}$C NMR are in agreement with the structure.

Example 14

(3aR,4R,5R,6aS)-Hexahydro-5-hydroxy-4-[(3R)-5-phenyl-3-hydroxypentyl]-2H-cyclopenta[b]furan-2-ol [11] ($C^1$—$C^2$ and $R^3$=$R^4$=H)

Scheme 19

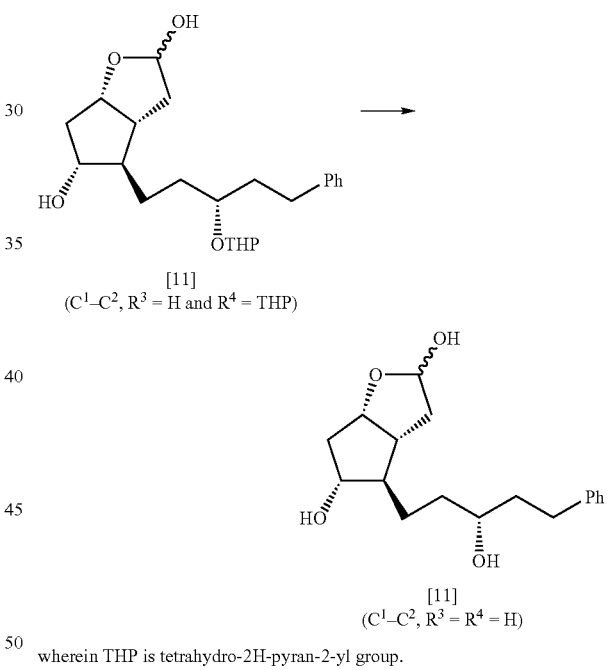

wherein THP is tetrahydro-2H-pyran-2-yl group.

A mixture of compound [11] ($C^1$—$C^2$, $R^3$=H and $R^4$=THP) (0.55 g), acetic acid (2 mL), THF (2 mL) and water (2 mL) was stirred at 40–50° C. for 4 hours (TLC monitoring). The mixture was basified with 1 N aq. potassium hydroxide to pH 10–11 and the product was extracted with dichloromethane (3×20 mL). The combined organic layers were dried over sodium sulfate, filtered and evaporated under reduced pressure. The residue was purified by column chromatography on silica gel (elution with gradient ethyl acetate/hexane from 1:2 to 3:1 v/v) to give 0.18 g (43%) of the compound [11] ($C^1$—$C^2$, $R^3$=$R^4$=H) as a colorless oil. $^1$H NMR (CD$_3$OD) is compatible with literature data.

Example 15

7-[(1R,2R,3R,5S)-3,5-dihydroxy-2-[(3R)-5-phenyl-3-[(tetrahydro-2H-pyran-2-yl)oxy]pentyl]cyclopentyl]-5Z-heptenoic acid [1a]($C^1$—$C^2$, $R^3$=H and $R^4$=THP)

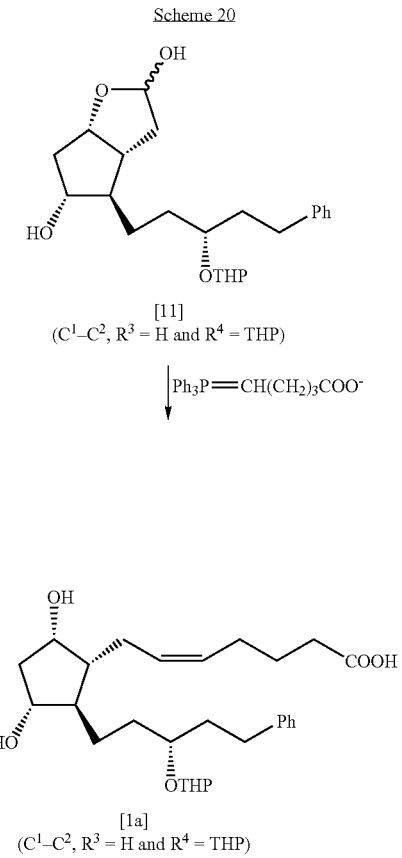

Potassium tert-butoxide (33.3 g) was added to a stirred suspension of (4-carboxybutyl)triphenylphosphonium bromide (66.0 g) in THF (200 mL) at 0–5° C. and the mixture was stirred at room temperature during 0.5 h. A solution of compound [11] ($C^1$—$C^2$, $R^3$=H and $R^4$=THP) (13.0 g) in THF (100 mL) was added dropwise during 2 hours to the resultant red orange suspension of potassium 5-(triphenylphosphoranylidene)pentanoate at −15° C. The mixture was stirred for 3 hours at this temperature (TLC monitoring) and poured into ice water (1 L). The alkaline solution was washed with t-BuOMe (4×500 mL), mixed with ether (500 mL) and acidified with 10% aqueous solution of citric acid to pH 4. The white precipitated crystals were filtered off and washed on filter with ether (200 mL). The ether layer was separated from combined filtrates. The water phase was extracted with ether (200 mL). The combined organic extracts were concentrated to a volume 400 mL, washed with water (5×200 mL), dried over sodium sulfate, filtered and evaporated under reduced pressure to give 13.5 g (86% yield) of the compound [1a]($C^1$—$C^2$, $R^3$=H and $R^4$=THP).

Example 16

7-[(1R,2R,3R,5S)-3,5-Dihydroxy-2-[(3S)-5-phenyl-3-[(tetrahydro-2H-pyran-2-yl)oxy]-1E-pentenyl]cyclopentyl]-5Z-heptenoic acid [1a]($C^1$=$C^2$, $R^3$=H and $R^4$=THP)

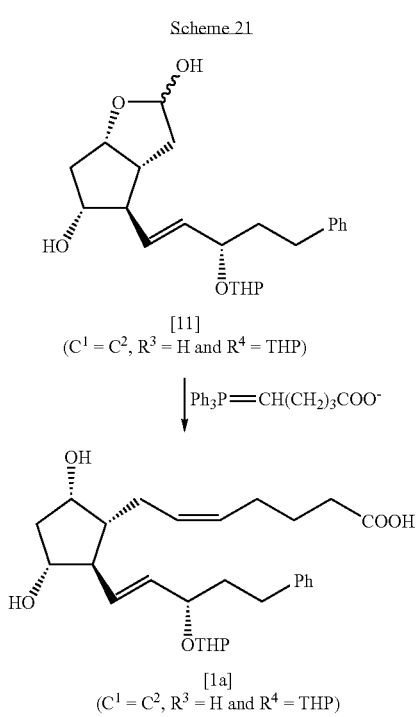

Potassium tert-butoxide (2.60 g) was added to a stirred suspension of (4-carboxybutyl)triphenylphosphonium bromide (5.14 g) in THF (50 mL) at 0–5° C. and the mixture was stirred at room temperature during 0.5 h. A solution of compound [11] ($C^1$=$C^2$, $R^3$=H and $R^4$=THP) (1.00 g) in THF (25 mL) was added dropwise to the resultant red orange suspension of potassium 5-(triphenylphosphoranylidene)pentanoate at −20—−15° C. The mixture was stirred for 8 hours at this temperature (TLC monitoring) and poured into ice water (100 mL). The alkaline solution was washed with t-BuOMe (4×50 mL), mixed with t-BuOMe (50 mL) and acidified with 5% aqueous solution of citric acid to pH 4–5. The white precipitated crystals were filtered off and washed on filter with t-BuOMe (20 mL). The water phase was extracted with t-BuOMe (20 mL). The combined organic extracts were kept overnight at −15° C. over sodium sulfate, filtered and evaporated under reduced pressure to give 1.1 g (91.7% yield) of the compound [1a]($C^1$=$C^2$, $R^3$=H and $R^4$=THP). $^1$H NMR (CDCl$_3$) δ: 7.16–7.26 (m, 5H), 5.20–5.50 (m, 4H); 4.65–4.75 (m, 1H); 4.10–4.25 (m, 1H); 3.40–4.10 (m, 7H); 1.25–2.68 (m, 21H).

Example 17

Latanoprost Acid

Scheme 22

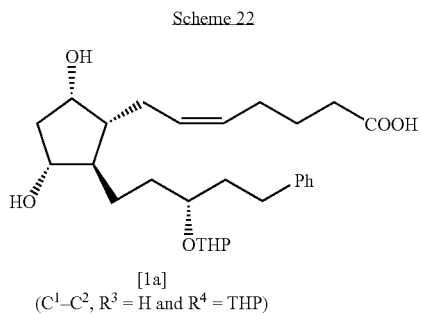

[1a]
(C¹–C², R³ = H and R⁴ = THP)

↓

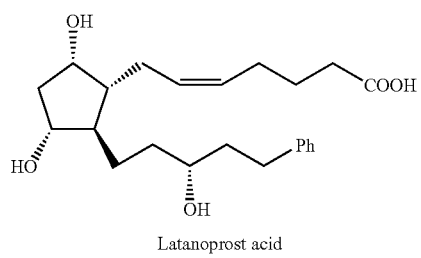

Latanoprost acid wherein THP is tetrahydro-2H-pyran-2-yl group

Pyridinium p-toluenesulfonate (70 mg) was added to a stirred solution of the compound [1a](C¹—C², R³=H and R⁴=THP) (1.8 g) in methanol (50 mL) at room temperature. The mixture was stirred at 50° C. over a period of 4 hours, by which time the reaction was complete (HPLC monitoring). The mixture was evaporated under reduced pressure. Water (10 mL) and ethanol (10 mL) were added to a residue. The mixture was basified with 1 N aq. NaOH to pH 12, stirred for 1 hour at 70–75° C. and evaporated under reduced pressure. A solution of the residue in water (50 mL) was extracted with ethyl acetate (5×20 mL), acidified with 10% aq. citric acid to pH 4 and extracted with ether (3×50 mL). The combined organic extracts were dried over sodium sulfate, filtered and evaporated under reduced pressure to give 1.35 g (96% yield) of Latanoprost acid as colorless oil. The crude Latanoprost acid may be purified by chromatography on silica gel (elution with hexane/ethyl acetate 1:1 v/v) or by crystallization its salts with tromethamine, histamine, L-arginine, triptamine or adamantanamine from various solvents following isolation of the purified Latanoprost acid from the salts.

Example 18

17-Phenyl-18,19,20-trinor-PGF$_{2\alpha}$

Scheme 23

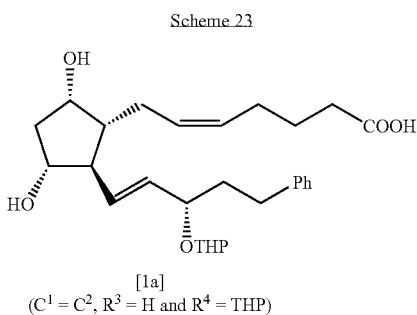

[1a]
(C¹ = C², R³ = H and R⁴ = THP)

↓

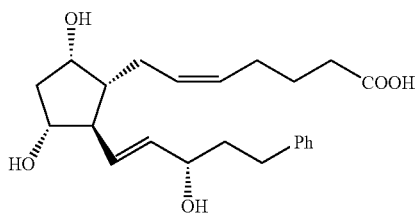

17-Phenyl-18, 19, 20-trinor-PGF$_{2\alpha}$ wherein THP is tetrahydo-2H-pyran-2-yl group.

Pyridinium p-toluenesulfonate (10 mg) was added to a stirred solution of the compound [1a](C¹=C², R³=H and R⁴=THP) (1.1 g) in methanol (25 mL) at room temperature. The mixture was stirred at 40–50° C. over a period of 3 hours, by which time the reaction was complete (HPLC monitoring). The mixture was evaporated under reduced pressure. A mixture of the residue and water (30 mL) was basified with 1 N aq. NaOH to pH 12 and extracted with ether (20 mL×5). The aqueous phase was acidified with 5% aq. citric acid to pH 4–5 and extracted with ether (3×30 mL). The combined organic extracts were dried over sodium sulfate, filtered and evaporated under reduced pressure to give 0.80 g (84% yield) of 17-phenyl-18,19,20-trinor-PGF$_{2\alpha}$. $^1$H NMR (CDCl$_3$) δ: 7.12–7.27 (m, 5H); 5.33–5.63 (m, 7H); 4.00–4.20 (m, 2H); 3.80–4.00 (m, 1H); 2.50–2.70 (m, 2H); 1.56–2.30 (m, 14H). $^{13}$C NMR (CDCl$_3$) δ: 24.5; 25.3; 26.3; 31.8; 33.0; 38.5; 42.8; 50.1; 55.2; 72.3; 72.5; 77.6; 125.8; 128.4; 129.2; 129.6; 133.1; 134.8; 141.9; 177.4.

Example 19

7-[(1R,2R,3R,5S)-3,5-Dihydroxy-2-[(3R)-5-phenyl-3-[(tetrahydro-2H-pyran-2-yl)oxy]pentyl]cyclopentyl]-5Z-heptenoic acid, isopropyl ester [1c]

Scheme 24

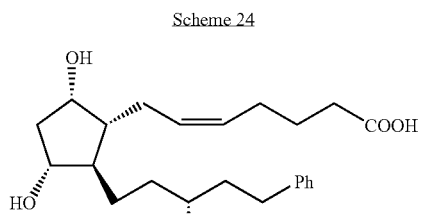

[1a]
(C$^1$–C$^2$, R$^3$ = H and R$^4$ = THP)

↓ i-PrI/Base

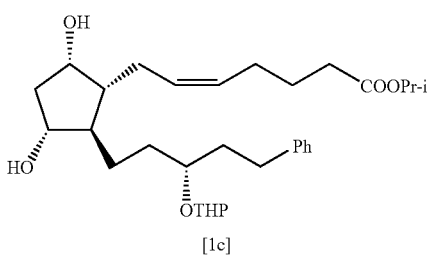

[1c]
wherein THP is tetrahydro-2H-pyran-2-yl group.

1,8-Diazabicyclo[5.4.0]undec-7-ene (3.73 g) was added dropwise to a stirred solution of compound [1a](C$^1$—C$^2$, R$^3$=H and R$^4$=THP) (1.66 g) in acetone (15 mL) at 0° C. The solution was warmed to room temperature, and isopropyl iodide (3.6 g) was added dropwise to it. The resulting mixture was stirred overnight at room temperature (TLC monitoring). The mixture was concentrated to a volume 5 mL, dichloromethane (70 mL) was added and the resulting mixture was washed with 3% aqueous solution of citric acid (2×20 mL), 5% aqueous solution of sodium bicarbonate (2×10 mL) and brine, dried over sodium sulfate, filtered and evaporated under reduced pressure. The residue (1.8 g) was purified by column chromatography on silica gel (eluent hexane/ethyl acetate 2:1 v/v) to obtain 1.3 g (72% yield) of the compound [1c]. $^1$H NMR (CDCl$_3$) δ: 7.14–7.29 (m, 5H); 5.27–5.46 (m, 2H); 4.91–5.03 (m, 1H); 4.58–4.64 (m, 1H); 4.07–4.13 (m, 1H); 3.71–3.92 (m, 2H); 3.66–3.71 (m, 1H); 3.45–3.50 (m, 1H); 1.19 (d, J=8 Hz, 6H). $^{13}$C NMR (CDCl$_3$) δ: 20.0; 20.4; 21.8; 25.0; 25.5; 26.7; 27.1; 29.1; 31.3; 32.0; 34.1; 36.7; 42.5; 51.8; 53.3; 62.9; 67.5; 74.8; 78.9; 97.8; 125.6; 125.8; 128.3; 128.4; 129.3; 129.5; 129.6; 143.0; 173.3.

Example 20

Latanoprost

Scheme 25

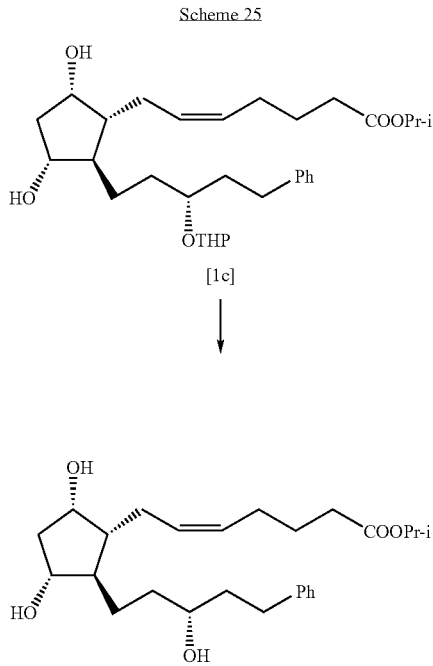

Latanoprost
wherein THP is tetrahydo-2H-pyran-2-yl group.

Pyridinium p-toluenesulfonate (16 mg) was added to a stirred solution of the compound [1c] (0.7 g) in ethanol (20 mL) at room temperature. The mixture was stirred at 50° C. over a period of 3 hours, by which time the reaction was complete (TLC monitoring). The mixture was concentrated under reduced pressure. The residue was diluted with dichloromethane (40 mL). The solution was washed with water (10 mL) and brine (10 mL), dried over sodium sulfate and evaporated under reduced pressure. The residue was purified by column chromatography on silica gel (hexane/ethyl acetate 1:1 v/v) to obtain Latanoprost. $^1$H NMR (CDCl$_3$) is compatible with literature data.

Example 21

Latanoprost

Scheme 26

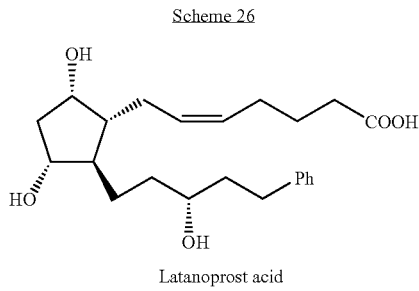

Latanoprost acid

↓ i-PrI/Cs$_2$CO$_3$

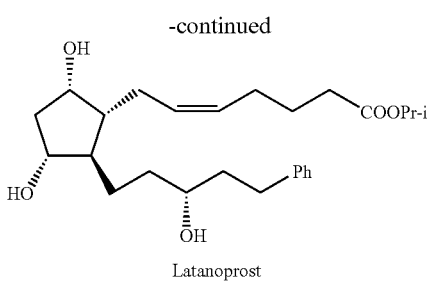

Latanoprost

A mixture of Latanoprost acid (0.95 g, 2.4 mmol), isopropyl iodide (0.83 g, 4.8 mmol), cesium carbonate (1.20 g, 3.6 mmol) and DMF (20 mL) was stirred for 2–3 hours at 40–50° C. (TLC monitoring) and poured into a stirred mixture of 2 M aqueous NaHSO$_4$ (2.5 mL, 5 mmol), ice (50 mL) and ether (50 mL). The organic layer was separated and the water phase was extracted with ether (2×50 mL). The combined organic layers were washed with brine (50 mL), dried over sodium sulfate, filtered and evaporated under reduced pressure to give 1.05 g (100% yield) of crude product. The crude product was purified by column chromatography on silica gel (hexane/ethyl acetate 1:1 v/v) to give Latanoprost. $^1$H NMR (CDCl$_3$) is compatible with literature data.

Example 22

Methyl ester of 17-phenyl-18,19,20-trinor-PGF$_{2\alpha}$ [1b] (C$^1$=C$^2$ and R$^6$=OMe)

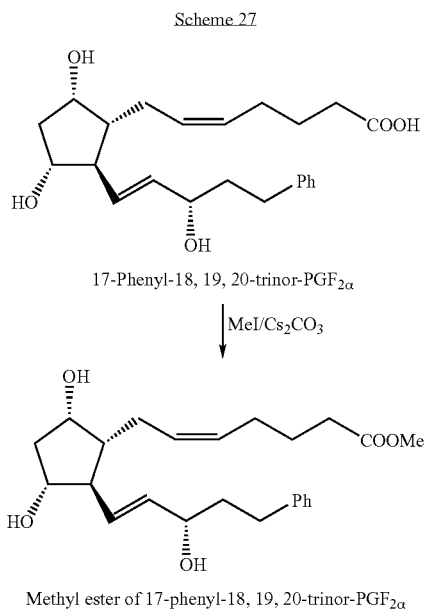

Scheme 27

17-Phenyl-18, 19, 20-trinor-PGF$_{2\alpha}$

| MeI/Cs$_2$CO$_3$

Methyl ester of 17-phenyl-18, 19, 20-trinor-PGF$_{2\alpha}$

A mixture of 17-phenyl-18,19,20-trinor-PGF$_{2\alpha}$ (2.7 g, 6.9 mmol), methyl iodide (1.48 g, 10.4 mmol), cesium carbonate (3.4 g, 10.4 mmol) and DMF (25 mL) was stirred for 3 hours at 0–10° C. (TLC monitoring) and poured into a stirred mixture of 2 M aqueous NaHSO$_4$ (5 mL, 1.0 mmol), ice (100 mL) and ether (50 mL). The organic layer was separated and the water phase was extracted with ether (4×100 mL). The combined organic layers were washed with 1 M aq. sodium thiosulfate and brine (3×50 mL), dried over sodium sulfate, filtered and evaporated under reduced pressure to give 2.7 g (96.4% yield) of crude product. The crude product was purified by column chromatography on silica gel (hexane/ethyl acetate 1:2 v/v) to give 2.6 g (93% yield) of methyl ester of 17-phenyl-18,19,20-trinor-PGF$_{2\alpha}$. $^1$H NMR (CDCl$_3$) δ: 7.10–7.25 (m, 5H); 5.33–5.55 (m, 4H); 4.00–4.20 (m, 4H); 3.80–4.00 (m, 2H); 3.58 (s, 3H); 2.60–2.70 (m, 2H); 1.30–2.30 (m, 14H). $^{13}$C NMR (CDCl$_3$) δ: 24.6; 25.2; 26.4; 31.6; 33.2; 38.6; 42.7; 49.6; 51.3; 55.2; 71.9; 72.2; 77.2; 125.6; 128.1; 128.2; 129.0; 129.2; 133.3; 135.2; 141.8; 174.1.

Example 23

Bimatoprost

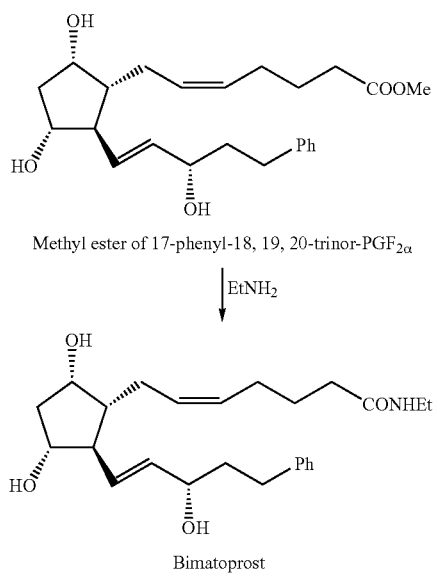

Scheme 28

Methyl ester of 17-phenyl-18, 19, 20-trinor-PGF$_{2\alpha}$

| EtNH$_2$

Bimatoprost

A mixture of methyl ester of 17-phenyl-18,19,20-trinor-PGF$_{2\alpha}$ (2.5 g, 6.2 mmol) and 70 wt. % aqueous ethylamine (100 mL) was stirred for 60 hours at 20–25° C. (TLC monitoring). A solution was concentrated under reduced pressure to half of a volume, neutralized with 2 M aqueous NaHSO$_4$ and extracted with ethyl acetate (5×100 mL). The combined organic layers were washed with brine (2×30 mL), dried over sodium sulfate, filtered and evaporated under reduced pressure. The residue was treated with ether (20 mL), precipitated solid was filtered off and dried under reduced pressure to give 2.1 g (81.7% yield) of Bimatoprost as white solid.

$^1$H NMR (CDCl$_3$) δ: 7.09–7.27 (m, 5H); 6.12 (t, J=5.5 Hz, 1H); 5.26–5.60 (m, 4H); 3.84–4.05 (m, 4H); 3.10–3.23 (m, 2H); 2.59–2.67 (m, 2H); 1.37–2.36 (m, 15H); 1.05 (t, J=7.3 Hz, 3H). $^3$C NMR (CDCl$_3$) δ: 14.6; 25.3; 25.5; 26.6; 31.7; 34.2; 35.7; 38.6; 42.8; 49.9; 55.2; 72.1; 77.3; 125.6; 128.2; 128.3; 129.1; 129.4; 133.1; 135.0; 141.9; 173.3.

Although certain presently preferred embodiments of the invention have been described herein, it will be apparent to those skilled in the art to which the invention pertains that variations and modifications of the described embodiments may be made without departing from the spirit and scope of the invention.

What is claimed is:

1. A process for the preparation of compound of Formula (1b)

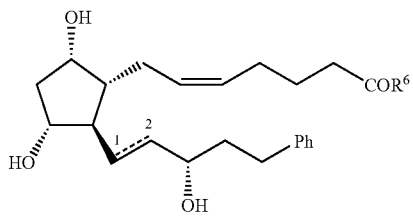

wherein $R^6$ is selected from the group consisting of alkoxy and alkylamino; such process comprising:

(a) stereoselective reduction of the carbonyl group of the compound (4)

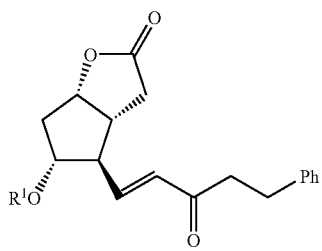

to yield a mixture of compounds of formulae (5a) and (6a),

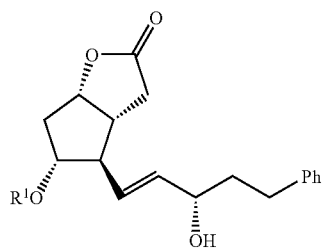

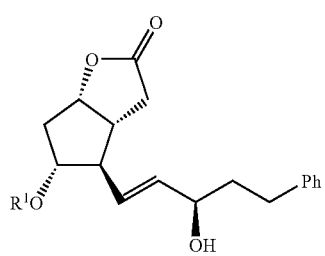

where (5a) is the predominant isomer, which are subsequently converted into a mixture of compounds of formulae (5) and (6):

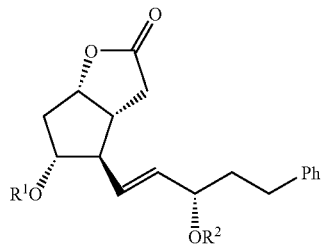

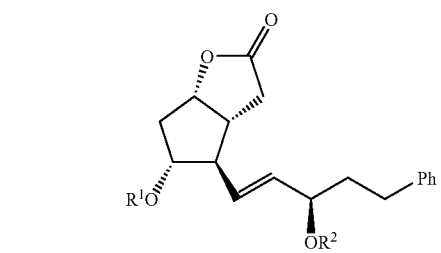

where one of $R^1$ and $R^2$ is an arylcarbonyl group and the other one is selected from the group consisting of arylcarbonyl, acyl, trialkylsilyl, dialkylarylsilyl, 1-alkoxyalkyl, unsubstituted and alkyl-substituted tetrahydro-2H-pyran-2-yl and tetrahydrofuran-2-yl; followed by isolation of the compound (5) from the mixture;

(b) converting compound (6) from the mother liquor of step (a) into compound (6a), oxidizing the hydroxyl group of the compound (6a) to yield the compound (4) and recycling the compound (4) to step (a);

(c) reducing the compound (5) with diisobutylaluminum hydride while maintaining the reaction mixture temperature in the range of from −20° C. to +20° C. followed by hydrolysis of the obtained reaction mixture under basic conditions to give the compound (11),

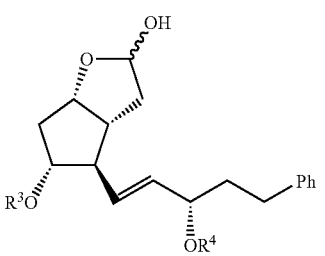

wherein $R^3$ is hydrogen when $R^1$ is acyl and is equal to $R^1$ when it is trialkylsilyl, dialkylarylsilyl, 1-alkoxyalkyl, unsubstituted or alkyl-substituted tetrahydro-2H-pyran-2-yl or tetrahydrofuran-2-yl; $R^4$ is hydrogen when $R^2$ is acyl and is equal to $R^2$ when it is trialkylsilyl, dialkylarylsilyl, 1-alkoxyalkyl, unsubstituted or alkyl-substituted tetrahydro-2H-pyran-2-yl or tetrahydrofuran-2-yl;

(d) reacting compound (11) with a metal salt of 5-(triphenylphosphoranylidene)pentanoic acid, to obtain the compound of formula (1a)

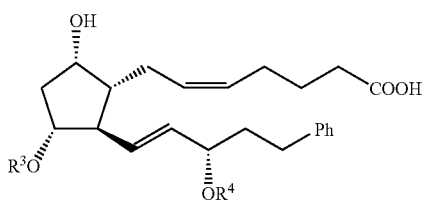
(1a)

and (e) alkylation or amidation of the carboxyl group of compound (1a), optionally, after deprotecting the hydroxyl groups, to give the desired compound (1b).

2. A process according to claim 1 wherein one of $R^1$ and $R^2$ is arylcarbonyl and the second one is selected from the group consisting of unsubstituted and alkyl-substituted tetrahydro-2H-pyran-2-yl and tetrahydrofuran-2-yl groups and arylcarbonyl group.

3. A process according to claim 1 wherein one of $R^1$ and $R^2$ is arylcarbonyl and the second one is selected from the group consisting of benzoyl, p-toluoyl, p-phenylbenzoyl (PPB) and tetrahydro-2H-pyran-2-yl (THP) groups and $R^6$ is a hydroxy, methoxy, isopropoxy or ethylamino group.

4. A process according to claim 1 wherein $R^1$ is p-phenylbenzoyl group and $R^2$ is tetrahydro-2H-pyran-2-yl (THP) group.

5. A process according to claim 1 wherein said stereoselective reduction of the carbonyl group of the compound (4) in step (a) is carried out by (−)-B-chlorodiisopinocampheylborane.

6. A process according to claim 1, which further comprises purifying the compound of formula (5) obtained in step (a) by re-crystallization.

7. A process for the preparation of compound of the formula [5] (5a)

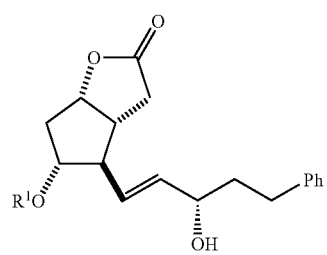
(5a)

which comprises reducing a compound of the formula (4)

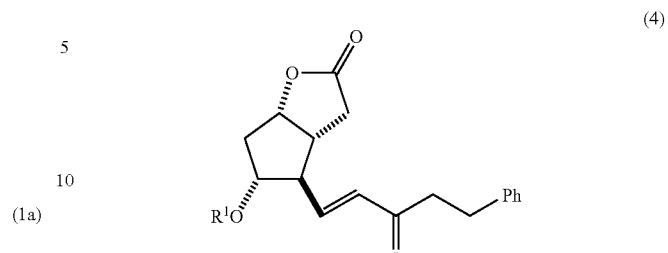
(4)

wherein $R^1$ is an aryl carbonyl group, with (−)-B-chlorodiisopinocampheylborane.

8. The process according to claim 7, wherein said process is maintained at a reaction mixture temperature in the range of from −50° C. to 20° C.

9. The process according to claim 7, further comprising the step of quenching said reduction with a boron complexing agent.

10. The process according to claim 8, wherein said boron complexing agent is methanol.

11. A process for the preparation of compound of the formula (5a):

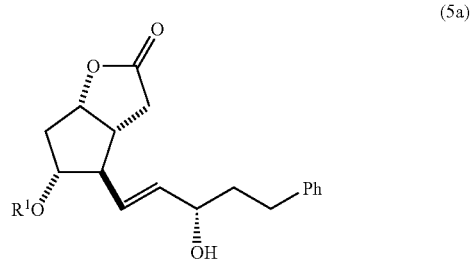
(5a)

which comprises the steps of:

(a) reducing a compound of the formula (4):

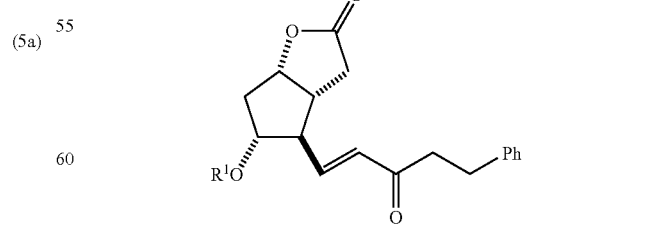
(4)

wherein $R^1$ is an aryl carbonyl group, with (−)-B-chlorodiisopinocampheylborane; and (b) quenching said reduction step.

12. The process according to claim 11, wherein said reduction is maintained at a reaction mixture temperature in the range of from about −50° C. to 20° C.

13. A process for the preparation of compound of the formula (5a):

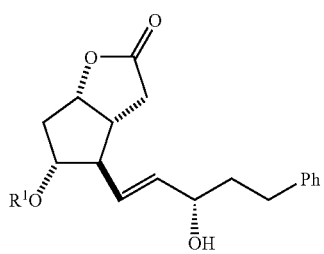

(5a)

which comprises the steps of:
(a) reducing a compound of the formula (4)

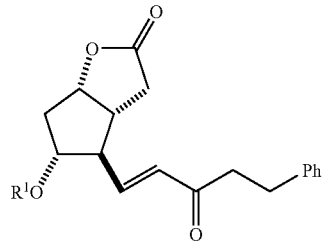

(4)

wherein $R^1$ is an aryl carbonyl group, with (−)-B-chlorodiisopinocampheylborane; while
  maintaining a reaction mixture temperature in the range of from −50°C. to 20° C.; and
(b) quenching said reduction step with a boron complexing agent.

14. The process according to claim 13, wherein said boron complexing agent is methanol.

* * * * *